US009585772B2

(12) United States Patent
Nomura et al.

(10) Patent No.: US 9,585,772 B2
(45) Date of Patent: Mar. 7, 2017

(54) STENT FOR MEDICAL USE

(71) Applicant: Olympus Corporation, Tokyo (JP)

(72) Inventors: Yusuke Nomura, Yokohama (JP);
Toshihiro Yamagata, Tokyo (JP);
Madoka Kiyokawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/318,053

(22) Filed: Jun. 27, 2014

(65) Prior Publication Data

US 2015/0005894 A1    Jan. 1, 2015

Related U.S. Application Data

(63) Continuation of application No. PCT/JP2013/082440, filed on Dec. 3, 2013.
(Continued)

(51) Int. Cl.
*A61F 2/82* (2013.01)
*A61F 2/848* (2013.01)
*A61F 2/04* (2013.01)

(52) U.S. Cl.
CPC .............. *A61F 2/848* (2013.01); *A61F 2/04* (2013.01); *A61F 2002/041* (2013.01); *A61F 2220/0016* (2013.01)

(58) Field of Classification Search
CPC ...... A61F 2/04; A61F 2/848; A61F 2002/041; A61F 2250/0012; A61F 2250/0018; A61F 2250/0029
See application file for complete search history.

(56) References Cited

U.S. PATENT DOCUMENTS 5,282,860 A * 2/1994 Matsuno ............... A61F 2/07
                                                    623/1.22
8,968,386 B2 * 3/2015 Svensson .............. A61F 2/89
                                                    623/1.16
(Continued)

FOREIGN PATENT DOCUMENTS

EP    2 564 818      3/2013
JP    A-05-192389    8/1993
(Continued)

OTHER PUBLICATIONS

Materials Data Book—Cambridge University Engineering Department; 2003 Edition; accessed at http://www-mdp.eng.cam.ac.uk/web/library/enginfo/cueddatabooks/materials.pdf.*
(Continued)

*Primary Examiner* — David Isabella
*Assistant Examiner* — Dinah Baria
(74) *Attorney, Agent, or Firm* — Oliff PLC

(57) ABSTRACT

A stent for medical use includes: a main body which includes a first rigid portion formed in a tubular shape along a longitudinal axis and having a predetermined rigidity with respect to a compression force exerted in a radial direction and a second rigid portion having a rigidity less than that of the first rigid portion, the second rigid portion which is substantially coaxial with and continues to a proximal end of the first rigid portion, and the second rigid portion which formed in a tubular shape along the longitudinal axis; and a gripping target region which is provided on an outer circumferential surface of the second rigid portion and is gripped by a gripping tool when the main body is led into a channel of an endoscope.

4 Claims, 14 Drawing Sheets

Related U.S. Application Data

(60) Provisional application No. 61/774,302, filed on Mar. 7, 2013, provisional application No. 61/774,290, filed on Mar. 7, 2013.

(56) References Cited

U.S. PATENT DOCUMENTS

| | | | |
|---|---|---|---|
| 2003/0088309 A1 | 5/2003 | Iwasaka et al. | |
| 2010/0256732 A1* | 10/2010 | Shin | A61F 2/90 623/1.15 |
| 2012/0095545 A1 | 4/2012 | Yamagata | |
| 2012/0330433 A1 | 12/2012 | Yamagata | |
| 2013/0073029 A1* | 3/2013 | Shaw | A61F 2/848 623/1.36 |

FOREIGN PATENT DOCUMENTS

| | | |
|---|---|---|
| JP | A-11-076412 | 3/1999 |
| JP | A-2007-524480 | 8/2007 |
| JP | A-2010-536430 | 12/2010 |
| JP | A-2010-537743 | 12/2010 |
| JP | B2-4981994 | 7/2012 |
| JP | B2-5124703 | 1/2013 |
| WO | 00/49973 A2 | 8/2000 |
| WO | WO 2005/072806 A2 | 8/2005 |
| WO | WO 2009/023720 A1 | 2/2009 |
| WO | WO 2009/029744 A1 | 3/2009 |
| WO | 2009/058369 A1 | 5/2009 |
| WO | WO 2011/118081 * | 9/2011 |
| WO | 2012/068508 A1 | 5/2012 |

OTHER PUBLICATIONS

Mar. 18, 2014 International Search Report issued in Application No. PCT/JP/2013082440 (including English Translation).

Oct. 7, 2014 Notice of Allowance issued in Japanese Application No. 2014-530844 (including English Translation).

Nov. 17, 2016 Search Report issued in European Patent Application No. 13877309.8.

* cited by examiner

STENT FOR MEDICAL USE

The present application is a Continuation of International Patent Application No. PCT/JP2013/082440, filed Dec. 3, 2013, claiming priority on U.S. Patent Provisional Application No. 61/774,290, filed on Mar. 7, 2013, and U.S. Patent Provisional Application No. 61/774,302, filed on Mar. 7, 2013, the contents of said US Patent Provisional Applications and said PCT Application being incorporated herein by reference.

BACKGROUND OF INVENTION

Field of the Invention

The present invention relates to a stent for medical use that is indwelled inside a bile duct or a pancreas duct for use.

Description of Related Art

In the related art, a stent for medical use (hereinafter, also referred to as a "stent") has been used to expand a narrowed area formed in a bile duct or a pancreas duct and maintain patency while being indwelled in the narrowed area.

Examples of such stents are known from Japanese Patent No. 4981994 and Japanese Unexamined Patent Application, First Publication No. H11-76412. The stent disclosed in Japanese Patent No. 4981994 includes a coil (a reinforcement portion) which is formed by winding a strand about an axis, an outer layer which is formed in a substantially tubular shape and is provided at the outer peripheral side of the coil to be coaxial with the coil, and an inner layer which is formed in a substantially tubular shape and is provided at the inner peripheral side of the coil to be coaxial with the coil.

Four flaps (locking members) are fixed to the outer layer at equiangular intervals about the axis and located at an outer circumferential surface of a portion serving as a distal end side portion when the stent is inserted into a bile duct. Each flap has elasticity. When the flap is pressed inward in the radial direction of the outer layer, the flap is received in a notch portion formed in the outer layer.

Even at an outer circumferential surface at a proximal end side of the outer layer, the four flaps are similarly fixed at equiangular intervals about the axis.

The strand of the coil is provided at the constant pitch in the axial direction from the distal end side in relation to a portion to which the distal end side flap is fixed to the proximal end side in relation to a portion to which the proximal end side flap is fixed.

When a stent with such a configuration is indwelled inside a bile duct, an endoscope is inserted from a mouth or the like into a patient's body cavity, and a distal end of the endoscope advances to the vicinity of a duodenal papilla. The stent is inserted into a channel through a forceps opening of the endoscope, and is inserted into the bile duct while the stent is observed fluoroscopically. When the stent reaches a narrowed area of the bile duct, the distal end side flap is closed while being pressed by the narrowed area and is received in the notch portion. When the distal end side flap advances beyond the narrowed area, the flap is opened due to the release of the pressure applied from the narrowed area to the flap. Accordingly, the distal end side flap is locked into the narrowed area. The proximal end side flap locks the duodenal papilla. In this state, the stent is indwelled inside the narrowed area for a predetermined period of time.

Since the stent is provided with the coil, it is possible to suppress the indwelled stent from being crushed in the radial direction. Accordingly, it is possible to maintain a space inside a tube conduit of the stent and to cause bile to easily flow through the narrowed area.

While the stent is indwelled in the narrowed area, a component such as bile accumulates on an inner peripheral surface of the stent, and hence the tube conduit thereof is narrowed. When this happens, the indwelled stent is collected to be replaced by a new stent. The collection of the stent is performed when the stent moves (erroneously moves) from the position at which it is indwelled.

The stent is mainly replaced by the following methods.

A first method is a method of gripping a stent with a gripping tool inserted through a channel of an endoscope and extracting the endoscope to an outside of a body along with the gripping tool gripping the stent. In this case, there is a need to insert an endoscope into a patient again in order to insert a new stent into a body cavity.

A second method is a method (TTS: Through The Scope) of gripping a stent with a gripping tool inserted through a channel of an endoscope and extracting the stent and the gripping tool to the outside of a body through a channel while the position of the endoscope is fixed. The second method has an advantage that a burden on the patient is small and an operator's burden is also small compared to the first method.

In the stent which is indwelled for a predetermined period, the tube conduit is narrowed, and hence the inside of the tube conduit is not easily gripped. For this reason, the proximal end side outer circumferential surface of the stent is gripped by a gripping tool or is squeezed and vibrated by a snare. In order to reliably hold the stent with the gripping tool or the snare, there is a case in which the gripping tool or the snare is locked to the center portion of the stent in relation to the proximal end side flap of the outer layer. In Japanese Patent No. 4981994, the stent which is indwelled for a predetermined period needs to be collected while the proximal end of the stent is gripped. When the stent is led into the channel, the held portion of the stent first enters the channel, and the distal end side portion and the proximal end side portion in relation to the held portion of the stent subsequently enter the channel. That is, the stent is led into the channel while being folded back at the held portion.

SUMMARY OF THE INVENTION

According to an aspect of the present invention, a stent for medical use including: a main body which includes a first rigid portion formed in a tubular shape along a longitudinal axis and having a predetermined rigidity with respect to a compression force exerted in a radial direction and a second rigid portion having a rigidity less than that of the first rigid portion, the second rigid portion which is substantially coaxial with and continues to a proximal end portion of the first rigid portion, and the second rigid portion which formed in a tubular shape along the longitudinal axis; and a gripping target region which is provided on an outer circumferential surface of the second rigid portion and is gripped by a gripping tool when the main body is led into a channel of an endoscope.

According to a second aspect of the present invention, in the stent for medical use according to the first aspect, the stent for medical use may further include a locking member which includes a proximal end portion continued to the second rigid portion and an extension portion extending from the proximal end portion toward an outside of the main body in the radial direction at substantially a center position of the second rigid portion in the longitudinal axis so as to be hooked to a tissue.

According to a third aspect of the present invention, in the stent for medical use according to the second aspect, the first rigid portion may be configured to be indwelled inside a bile duct or a pancreas duct and the second rigid portion may be configured to protrude from a duodenal papilla into a lumen of a duodenum and may be configured to be indwelled inside one of the bile duct and the pancreas duct when the locking member is locked to the duodenal papilla.

According to a fourth aspect of the present invention, in the stent for medical use according to the second aspect, the first rigid portion may include a first resinous portion formed of a resin material in a tubular shape and a first reinforcement portion fixed to the first resinous portion to maintain the tubular shape of the first resinous portion. The second rigid portion may include a second resinous portion which continues to a proximal end portion of the first resinous portion and the second rigid portion is substantially coaxial with a proximal end of the first resinous portion and formed of a resin material in a tubular shape.

According to a fifth aspect of the present invention, in the stent for medical use according to the fourth aspect, the first reinforcement portion may be formed in a tubular shape and may be formed inside the first resinous portion to be coaxial with the first resinous portion. The first reinforcement portion may be formed of a material having an elastic modulus greater than the first resinous portion. The proximal end portion of the locking member may be provided at a middle portion of the second rigid portion in a direction along the longitudinal axis of the second rigid portion.

According to a sixth aspect of the present invention, in the stent for medical use according to the fourth aspect, a length from a first end of the second rigid portion which is positioned opposite to the first rigid portion to the proximal end portion of the locking member in a direction along the longitudinal axis may be equal to or shorter than a length from the proximal end portion of the locking member to an end of the second rigid portion which is positioned at a first rigid portion side.

According to a seventh aspect of the present invention, in the stent for medical use according to the second aspect, the first rigid portion may include a first resinous portion formed of a resin material in a tubular shape and a first reinforcement portion fixed to the first resinous portion to maintain the tubular shape of the first resinous portion. The second rigid portion may include a second resinous portion which continues to a proximal end portion of the first resinous portion and the second resinous portion is a substantially coaxial with a proximal end portion of the first resinous portion and formed of a resin material in a tubular shape and a second reinforcement portion fixed to a part of the second resinous portion in a circumferential direction about the longitudinal axis of the second resinous portion.

According to an eighth aspect of the present invention, in the stent for medical use according to the seventh aspect, the first reinforcement portion may be formed in a tubular shape and may be provided inside the first resinous portion to be coaxial with the first resinous portion. The second reinforcement portion may be provided inside the second resinous portion and may be coaxial with the second resinous portion. The first reinforcement portion may be formed of a material having an elastic modulus greater than that of the first resinous portion in a tubular shape, the first reinforcement portion may be provided to be coaxial with the first resinous portion in a range from a boundary position at a connection position between the first rigid portion and the second rigid portion to a second end of the first rigid portion which is positioned opposite to the second rigid portion in a direction along the longitudinal axis of the first resinous portion. The second reinforcement portion may be formed of a material having an elastic modulus greater than that of the second resinous portion. The second reinforcement portion may be provided in a range from a first end of the second rigid portion which is opposite to the first rigid portion in the second rigid portion to the boundary position in the direction along the longitudinal axis.

According to a ninth aspect of the present invention, in the stent for medical use according to the seventh aspect, the second reinforcement portion may be provided at a position not overlapping the locking member in the circumferential direction when viewed in a direction along the longitudinal axis.

According to a tenth aspect of the present invention, in the stent for medical use according to the seventh aspect, the second reinforcement portion may be formed in a plate shape extending in a direction along the longitudinal axis.

According to an eleventh aspect of the present invention, in the stent for medical use according to the seventh aspect, the second reinforcement portion may be formed in a bar shape extending in a direction along the longitudinal axis.

According to a twelfth aspect of the present invention, in the stent for medical use according to the eleventh aspect, a plurality of the locking members may be provided at an interval about the longitudinal axis. A plurality of the second reinforcement portions may be provided between the locking members adjacent in the circumferential direction with an interval in the circumferential direction and may be located at a position not overlapping the locking member in the circumferential direction when viewed in the direction along the longitudinal axis.

According to a thirteenth aspect of the present invention, in the stent for medical use according to the seventh aspect, the first reinforcement portion may be a coil formed by winding a first strand about the longitudinal axis. The second reinforcement portion may be formed by winding a second strand in a spiral shape about the longitudinal axis. The coil and the second reinforcement portion may be integrally formed with each other.

According to a fourteenth aspect of the present invention, in the stent for medical use according to the seventh aspect, the second reinforcement portion may be connected to the first reinforcement portion.

According to a fifteenth aspect of the present invention, in the stent for medical use according to the seventh aspect, a plurality of the second reinforcement portions may be provided at a part of the second resinous portion with an interval in the circumferential direction about the longitudinal axis.

According to a sixteenth aspect of the present invention, in the stent for medical use according to the first aspect, the first rigid portion may include a first resinous portion formed of a resin material in a tubular shape and a first reinforcement portion fixed to the first resinous portion to maintain the tubular shape of the first resinous portion. The second rigid portion may include a second resinous portion which continues to a proximal end of the first resinous portion and the second rigid portion may be substantially coaxial with a proximal end portion of the first resinous portion and may be formed of a resin material in a tubular shape and a second reinforcement portion fixed to the second resinous portion to maintain the tubular shape of the second resinous portion. The second reinforcement portion may have rigidity less than that of the first reinforcement portion.

In the medial stent according to a seventeenth aspect of the present invention, in the stent for medical use according to the sixteenth aspect, each of the first reinforcement portion and the second reinforcement portion may be a coil formed by winding a strand in a spiral shape about the longitudinal axis. A pitch of the strand in the second reinforcement portion may be larger than that of the strand in the first reinforcement portion.

In the medial stent according to an eighteenth aspect of the present invention, in the stent for medical use according to the seventeenth aspect, a wall portion of the second resinous portion may be provided with a gap which is formed in the thickness direction of the wall portion in a range from the proximal end portion of the locking member to an end of the second rigid portion which is positioned at a first rigid portion side in a direction along the longitudinal axis. The strand of the second reinforcement portion may be disposed inside the gap, the strand of the second reinforcement portion may be movable in a direction along the longitudinal axis with respect to the second resinous portion.

DETAILED DESCRIPTION OF THE INVENTION

Hereinafter, a first embodiment of a stent according to the present invention will be described with reference to FIGS. 1 to 8. Furthermore, in all of the drawings below, the scales of the thicknesses and the dimensions of the components are appropriately changed and shown in order for the drawings to be easily understood.

(First Embodiment)

Figure 1:
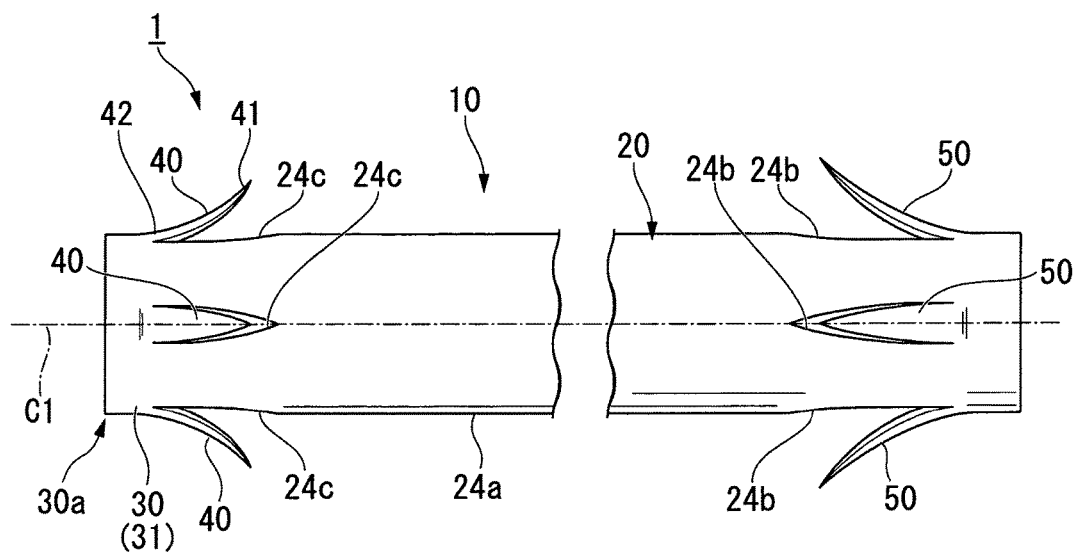
FIG. 1 is a side view showing a stent for medical use according to a first embodiment of the present invention.
Figure 2:
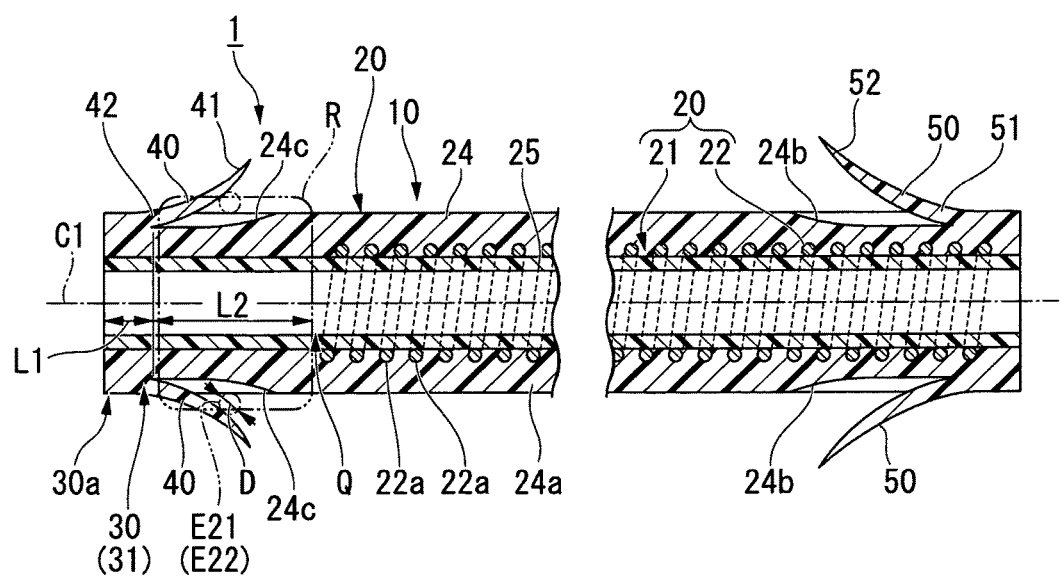
FIG. 2 is a side cross-sectional view showing the stent for medical use according to the first embodiment of the present invention.

As shown in FIGS. 1 and 2, a stent 1 (a stent for medical use) according to the embodiment includes a main body 10 which includes a first rigid portion 20, a second rigid portion 30 and a flap (a locking member) 40. The first rigid portion 20 and the second rigid portion 30 are formed in a tubular shape along a longitudinal axis C1. The flap 40 includes an extension portion 41 which extends outward in a radial direction of the main body 10 and a proximal end portion 42 which is connected to the extension portion 41 and is fixed to the second rigid portion 30.

The first rigid portion 20 includes a first resinous portion 21 which is formed in a tubular shape and a coil (a first reinforcement portion) 22 which is firmly fixed to the first resinous portion 21.

The first resinous portion 21 includes a distal end portion of an outer layer 24 which is formed in a tubular shape and a distal end portion of an inner layer 25 which is formed in a tubular shape and is formed at an inner circumferential side of the outer layer 24 to be coaxial with the outer layer 24.

The outer layer 24 is formed of a resin material such as urethane or polyethylene having elasticity, flexibility, and biocompatibility. The outer layer 24 has, for example, an outer diameter of 3.2 mm (10 French) and a length of 100 mm. The outer layer 24 is formed not only at the outer circumferential surface side of the coil 22, but also at a gap between strands 22a in the coil 22 to be described later.

In the embodiment, four flaps 50 are formed at the end portion opposite to the second rigid portion 30 in the outer layer 24 that serves as a distal end side portion when the stent is inserted into a bile duct (one flap 50 is not shown). The flap 50 is formed by notching a part of the outer layer 24 in the longitudinal direction and raising the notched portion. That is, the material of the flap 50 is the same as that of the outer layer 24. Four flaps 50 are formed at equiangular intervals about the longitudinal axis C1. Each flap 50 is formed so that a first end portion 51 is fixed to an outer circumferential surface of an end portion (first end) opposite to the second rigid portion 30 in the outer layer 24 and a second end portion 52 is opened outward in the radial direction of the main body 10 while extending along the longitudinal axis C1 toward a center portion 24a of the outer layer 24.

A notch portion 24b is formed in the outer circumferential surface of a position corresponding to each flap 50 in the outer layer 24. When the flap 50 is pressed from the outside in the radial direction toward the longitudinal axis C1, the flap 50 is received in the notch portion 24b.

The inner layer 25 is formed of a resin material such as PTFE (polytetrafluoroethylene) or PFA (perfluoroalkoxy alkane) having a smooth surface and biocompatibility. The inner layer 25 and the outer layer 24 are fixed to each other by thermal welding or the like.

The coil 22 is formed by winding the strand 22a about the longitudinal axis C1 in a spiral shape at the same pitch. The coil 22 is formed in a tubular shape as a whole by winding the strand 22a once or more. The strand 22a is formed of tungsten steel or stainless steel having a radiopaque property. The strand 22a is formed of metal having an elastic modulus (tensile strength) greater than that of the outer layer 24 and the inner layer 25. The cross-section of the strand 22a perpendicular to the longitudinal direction is formed in a circular shape. In the embodiment, the outer diameter of the strand 22a is, for example, 0.11 mm. The pitch of the strand 22a in a direction along the longitudinal axis C1 is, for example, about 0.41 mm (the gap between the strands 22a is about 0.30 mm). The strand 22a of the coil 22 is fixed (firmly fixed) to the outer layer 24 and the inner layer 25.

The coil 22 is formed at the boundary portion between the outer layer 24 and the inner layer 25 so as to be coaxial with the first resinous portion 21. That is, the coil 22 is formed inside the first resinous portion 21 to be located at, for example, substantially the center portion in the radial direction. In the first rigid portion 20, the coil 22 is formed to maintain the tubular shape of the first resinous portion 21. The first rigid portion 20 has a predetermined rigidity with respect to a compression force in the radial direction. The rigidity mentioned herein mainly indicates the resisting force with respect to a force of crushing the stent in the radial direction.

The second rigid portion 30 is formed in a tubular shape along the longitudinal axis C1. The second rigid portion 30 includes a second resinous portion 31 which is formed of a resin material in a tubular shape. The second resinous portion 31 includes a proximal end portion of the outer layer 24 and a proximal end portion of the inner layer 25. The second resinous portion 31, i.e., the second rigid portion 30, is connected to a proximal end of the first resinous portion 21 in a substantially coaxial state (also a coaxial state). Since the second rigid portion 30 does not include the coil 22, the rigidity thereof is less than that of the first rigid portion 20. The second rigid portion 30 is connected to the first rigid portion 20 so that the second rigid portion 30 is substantially coaxially with and continues to the proximal end portion of the first rigid portion 20 at a proximal end portion side of the first rigid portion 20.

Four flaps 40 are formed at the end portion opposite to the first rigid portion 20 in the outer layer 24 and disposed at the distal end side when the stent is inserted into a bile duct (one flap 40 is not shown). Each flap 40 is formed by notching and raising a part of the outer layer 24. That is, the material of the flap 40 is the same as that of the outer layer 24. Four flaps 40 are formed at equiangular intervals about the longitudinal axis C1.

The flap 40 includes the extension portion 41 and the proximal end portion 42. The flap 40 is formed so that the proximal end portion 42 is fixed to an outer circumferential surface of a first end 30a opposite to the first rigid portion 20 in the second resinous portion 31. The flap 40 is formed so that the extension portion 41 is opened outward in the radial direction of the main body 10 while extending along the longitudinal axis C1 toward the center portion 24a of the outer layer 24. The proximal end portion 42 of the flap 40 is fixed to the second rigid portion 30 at the middle portion of the second rigid portion 30 in the longitudinal axis C1. The extension portion 41 is disposed at substantially a center position of the second rigid portion 30 in the direction along the longitudinal axis C1.

A first length L1 from the first end 30a opposite to the first rigid portion 20 in the second rigid portion 30 to the proximal end portion 42 of the flap 40 in the direction along the longitudinal axis C1 is, for example, 5 mm.

A notch portion 24c is formed in the outer circumferential surface corresponding to each flap 40 in the outer layer 24. When the flap 40 is pressed from the outside of the radial direction toward the longitudinal axis C1, the flap 40 is received in the notch portion 24c.

The flap 40 is shorter than the flap 50. Since the flap 40 at the proximal end side (the duodenum side) is short, a smooth treatment may be performed by suppressing the flap 40 from being caught by a forceps raising base at an exit of an endoscope.

Here, a boundary position Q is defined as a connection position between the first rigid portion 20 and the second rigid portion 30 in the direction along the longitudinal axis C1. The boundary position Q is a portion at which the end of the coil 22 at the proximal end side is located.

The coil 22 is provided in the range from the boundary position Q to the end portion opposite to the second rigid portion 30 in the first rigid portion 20 while the coil is not provided from the boundary position Q toward the second rigid portion 30. In this example, a second length L2 from the proximal end portion 42 of the flap 40 to the boundary position Q is, for example, 7 mm. That is, the first length L1 from the first end 30a of the second rigid portion 30 to the proximal end portion 42 of the flap 40 is equal to or shorter than the second length L2.

The first length L1 is preferable short since the proximal end portion of the stent 1 protrudes from a duodenal papilla to a lumen of a duodenum when the stent is indwelled. However, when the flap 40 is fixed to the outer layer 24 by thermal welding or the like, it is preferable to ensure the first length L1 of 4 mm or more in order to also ensure fixing strength. The second length L2 is preferable set to be equal to or longer than 2 mm and equal to or shorter than 8 mm.

In the stent 1 according to the embodiment, each of the first rigid portion 20 and the second rigid portion 30 has a substantially uniform rigidity regardless of the position in the direction along the longitudinal axis C1. Then, since the rigidity of the first rigid portion 20 is greater than the rigidity of the second rigid portion 30, the rigidity largely changes at the boundary position Q.

In the description below, the range from the center portion 24a side of the proximal end portion 42 of the flap 40 in the second rigid portion 30 to the boundary position Q is indicated as a gripping target region R.

Next, the action of the stent 1 with the above-described configuration will be described below by exemplifying an operation in which the stent 1 is indwelled in a bile duct and the indwelled stent 1 is replaced.

Figure 3:
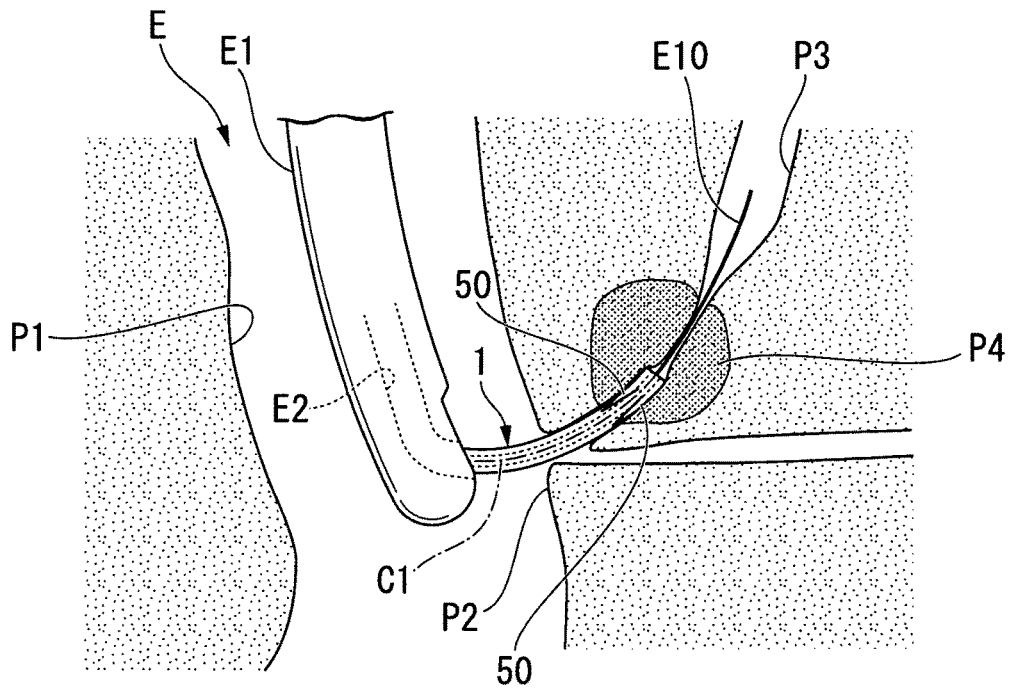
FIG. 3 is a view showing a procedure of indwelling the stent for medical use according to the first embodiment of the present invention.

First, a user such as an operator inserts a lateral vision type endoscope from a natural opening such as a mouth into a patient's body cavity, and causes a distal end of an insertion portion E1 of an endoscope E to advance to the vicinity of a duodenal papilla (a tissue) P2 through a duodenum P1 as shown in FIG. 3.

Next, the user inserts a guide wire E10 from a forceps opening (not shown) of the endoscope E into a channel E2, and causes a distal end of the guide wire E10 to protrude from a distal end opening of the channel E2 toward the duodenal papilla P2 while appropriately operating a raising table (not shown). Then, the distal end of the guide wire E10 is inserted from the duodenal papilla P2 into a bile duct P3.

Further, the user checks the shapes of a narrowed area P4 of the bile duct P3 and the duodenal papilla P2 using fluoroscopy, and selects the stent 1 having a proper length. That is, the stent 1 in which the length from the extension portion 41 of the flap 40 to the second end portion 52 of the flap 50 is longer than the length from the duodenal papilla P2 to the narrowed area P4 of the bile duct P3 when the flaps 40 and 50 are opened is selected.

Next, the user inserts the stent 1 into the bile duct P3 from the flap 50 along the guide wire E10 by a stent delivery catheter (not shown) inserted from the forceps opening while checking the positions and the shapes of the stent 1 and the bile duct P3.

Figure 4:
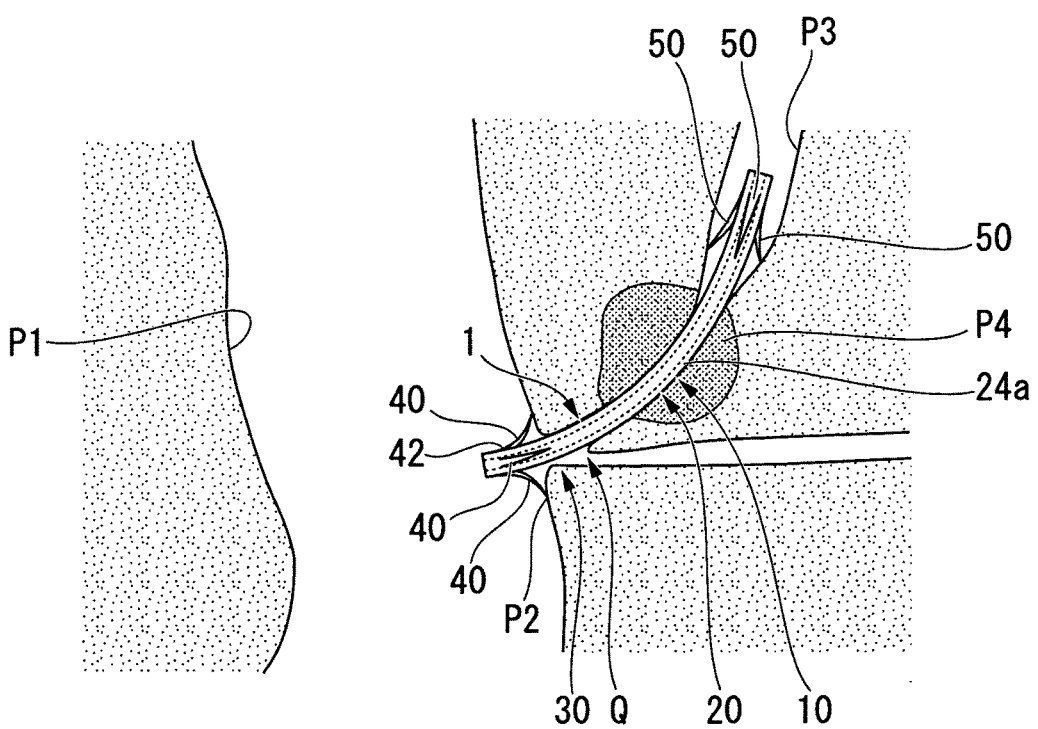
FIG. 4 is a view showing a procedure of indwelling the stent for medical use according to the first embodiment of the present invention.

When a distal end of the stent 1 reaches the narrowed area P4 of the bile duct P3, the flap 50 is pressed toward the longitudinal axis C1 by the narrowed area P4, and the flap 50 is received in the notch portion 24b. When the stent 1 is further inserted into the bile duct P3 and the flap 50 advances beyond the narrowed area P4, the second end portion 52 of the flap 50 is opened and the flap 50 is locked to the narrowed area P4 as shown in FIG. 4.

At this time, since the stent 1 in which the length from the extension portion 41 of the flap 40 to the second end portion 52 of the flap 50 is set to the above-described length is selected, the flap 40 is also locked to the duodenal papilla P2. Accordingly, at least a proximal end of the second rigid portion 30 protrudes from the duodenal papilla P2 into a lumen of the duodenum P1 to be indwelled therein. In other words, an outer circumferential surface of the main body 10 which is slightly the center portion 24a side from the proximal end portion 42 of the flap 40 protrudes into the lumen of the duodenum P1 in the indwelled state. Meanwhile, the first rigid portion 20 is indwelled inside the bile duct P3.

The boundary position Q of the stent 1 is located in the vicinity of the duodenal papilla P2. That is, the second rigid portion 30 is located substantially inside the duodenum P1. Thus, a space inside a tube conduit of a portion which is pressed by the bile duct P3 or the like in the stent 1 is maintained by the coil 22.

Next, the user extracts the guide wire E10 and the insertion portion E1 of the endoscope E from the patient's body cavity, and ends the operation of indwelling the stent 1. Next, when the stent 1 is indwelled for a predetermined period of time, the indwelled stent 1 is replaced by a new stent 1, as will be described later.

Figure 5:
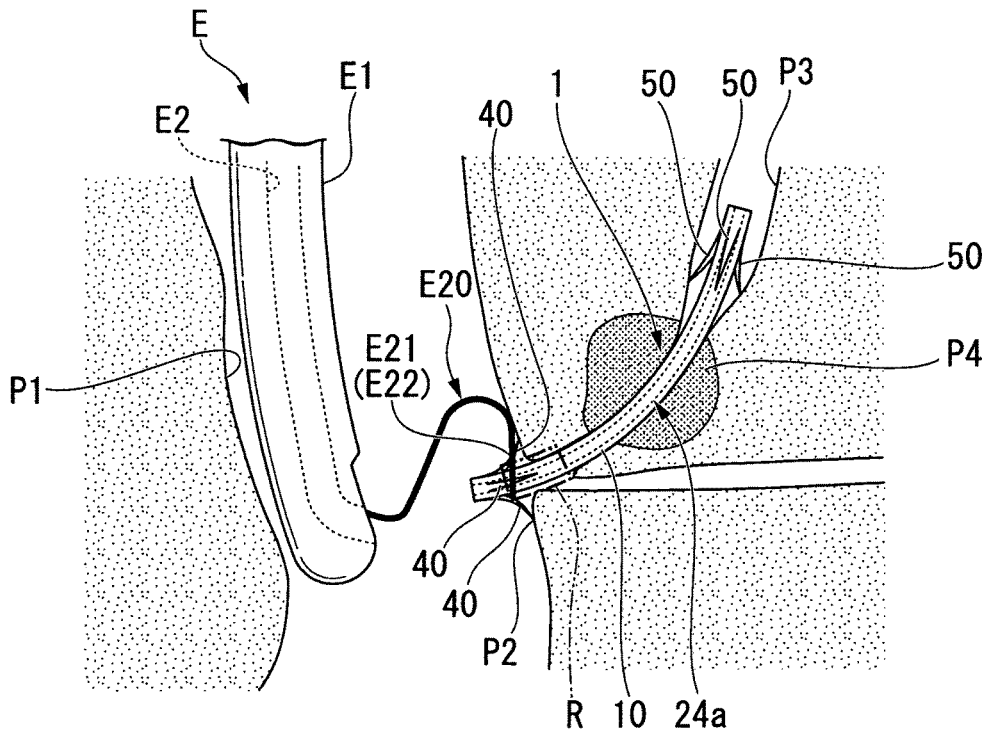
FIG. 5 is a view showing a procedure of replacing the indwelled stent for medical use of the first embodiment of the present invention.

First, as described above, the user inserts a distal end of the insertion portion E1 of the endoscope E in the vicinity of the duodenal papilla P2 through the duodenum P1 as shown in FIG. 5.

A snare E20 is inserted through the channel E2 from the forceps opening. As the snare E20 used at this time, a snare in which an outer diameter D (see FIG. 2) of a wire E22 forming a loop portion E21 of the snare E20 is sufficiently smaller than the second length L2 is selected as a snare used at this time. Furthermore, the loop portion E21 is formed by forming the wire E22 in a loop shape.

The snare E20 is pressed into the forceps opening, and the loop portion E21 is caused to protrude from the distal end opening of the channel E2. The loop portion E21 is hooked to the gripping target region R of the stent 1 through the proximal end of the stent 1 in the loop portion E21. More specifically, the loop portion E21 is hooked to the outer circumferential surface of the main body 10 which is slightly close to the center portion 24a in relation to the proximal end portion 42 of the flap 40.

When the snare E20 is pulled back while the position of the insertion portion E1 is fixed, the loop portion E21 is locked to the center portion 24a of the proximal end portion 42 of the flap 40 in the main body 10 as shown in FIGS. 2 and 5. Accordingly, the stent 1 is held in the snare E20. Since the outer diameter D of the wire E22 is sufficiently smaller than the second length L2, the wire E22 is apart from the boundary position Q in the direction along the longitudinal axis C1.

Figure 6:
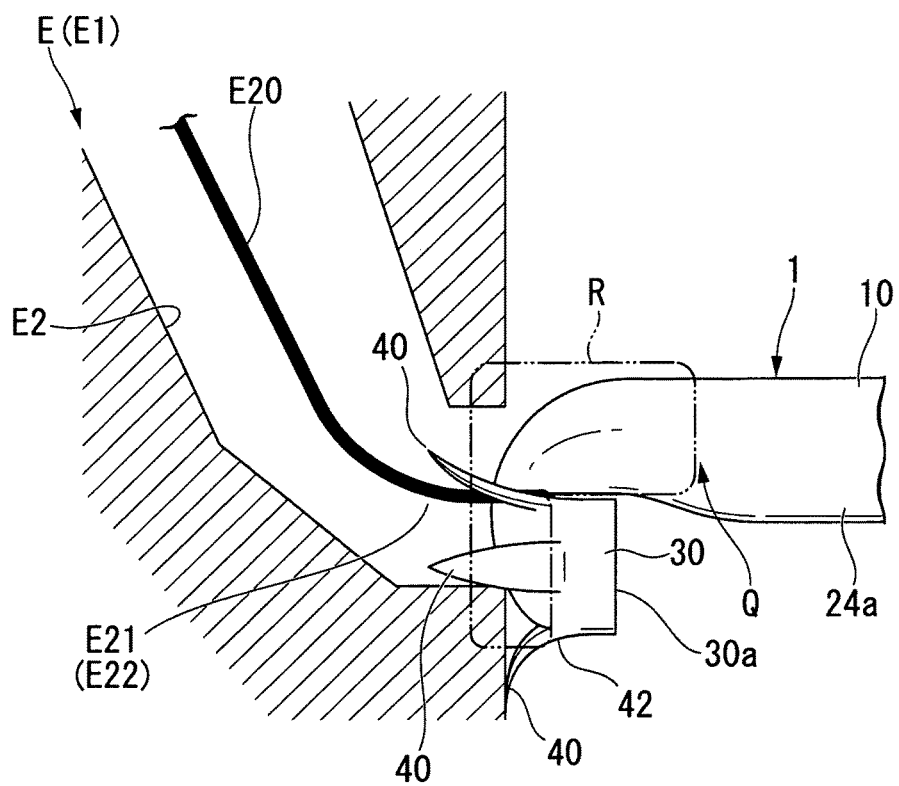
FIG. 6 is a view showing a procedure of replacing the indwelled stent for medical use of the first embodiment of the present invention.
Figure 7:
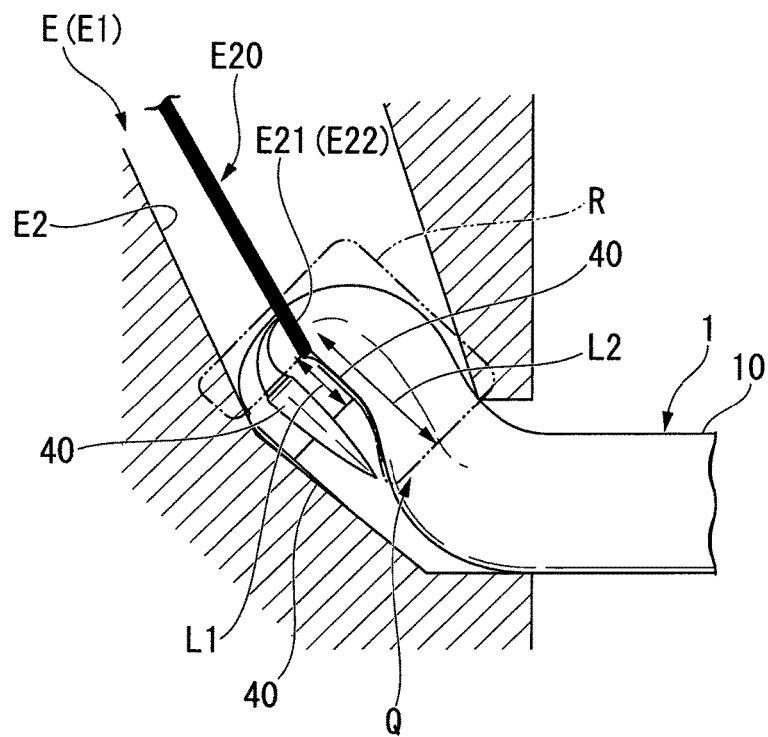
FIG. 7 is a view showing a procedure of replacing the indwelled stent for medical use of the first embodiment of the present invention.
Figure 8:
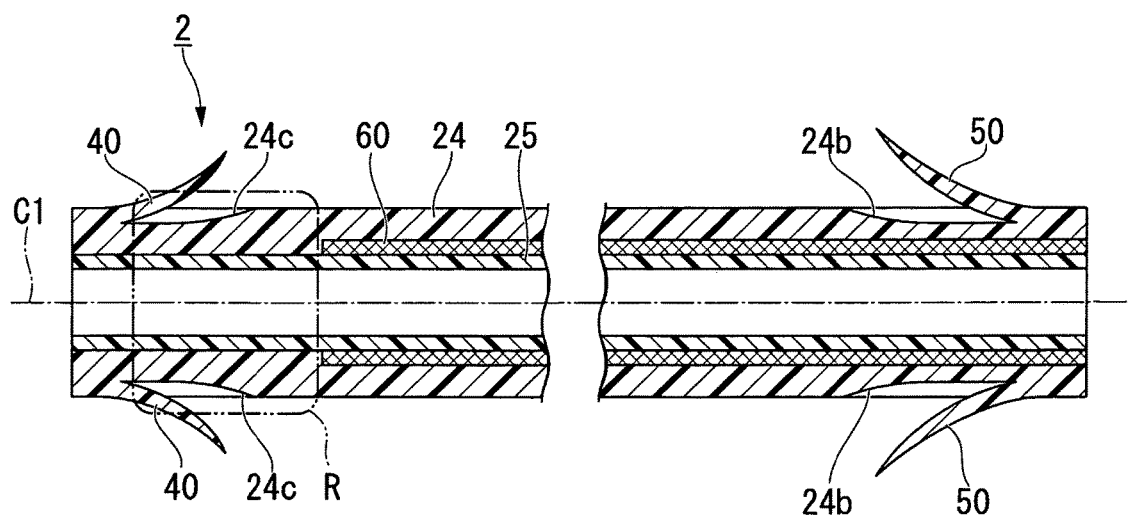
FIG. 8 is a side cross-sectional view showing a stent for medical use of a modified example of the first embodiment of the present invention.

When the snare E20 is pulled back, the stent 1 is extracted from the bile duct P3 and the stent 1 is led into the channel E2 of the insertion portion E1 as shown in FIG. 6. At this time, the held gripping target region R of the stent 1 first enters the channel E2, and a distal end side portion in relation to the gripping target region R in the stent 1 and the first end 30a of the second rigid portion 30, which is a proximal end side portion, subsequently enter the channel E2. That is, the stent 1 is led into the channel E2 while being folded back at the gripping target region R. Since the outer diameter of the stent 1 increases as a whole in a portion in which the stent 1 is folded back, the stent 1 is crushed in the radial direction when the stent is led into the channel E2 as shown in FIG. 7.

Since the first length L1 is shorter than the second length L2, the coil 22 is not provided in any part of the portion in which the stent 1 is folded back in the overlapping state. For this reason, the outer diameter of the overlapping portion easily decreases. Since the wire E22 is apart from the boundary position Q, an excessive force causing the wire E22 to dig into the boundary position Q of the stent 1 is not exerted on the boundary position Q of the stent 1. When the portion in which the stent 1 is folded back in the overlapping state passes through the channel E2, the other portions of the stent 1 also pass through the channel E2 together.

In this way, the snare E20 is pulled back while the position of the insertion portion E1 is fixed, and the stent 1 and the snare E20 are extracted to an outside of the body through the channel E2. Subsequently, the guide wire E10 is inserted into the channel E2, and a new stent 1 is indwelled inside the bile duct P3 through the channel E2 as described above.

According to the stent 1 of the embodiment, since the rigidity of the first rigid portion 20 is greater than that of the second rigid portion 30, a space inside a tube conduit in a portion which is pressed by the bile duct P3 or the like in the indwelled state is maintained. Since the rigidity of the second rigid portion 30 is less than that of the first rigid portion 20, the gripping target region R, where is a portion first led into the channel E2 and is a part of the second rigid portion 30, is easily crushed, i.e., deformed, when the stent 1 passes through the channel E2 for the stent 1 to be collected.

Since the outer diameter D of the wire E22 of the snare E20 is selected as described above, the wire E22 is apart from the boundary position Q when the loop portion E21 is locked to the proximal end portion 42 of the flap 40. Thus, it is possible to suppress a problem in which the main body 10 is torn and broken at the boundary position Q when an excessive force is exerted on the boundary position Q where the rigidity of the stent 1 largely changes.

The first length L1 from the first end 30a of the second rigid portion 30 to the proximal end portion 42 of the flap 40 is equal to or shorter than the second length L2 from the proximal end portion 42 of the flap 40 to the boundary position Q. Accordingly, when the stent 1 is led into the channel E2 of the insertion portion E1, the stent is folded back at the gripping target region R, and the coil 22 is not in the portion which is folded back in the overlapping state. For this reason, the overlapping portion may be easily crushed, that is, deformed. Thus, it is possible to suppress an increase in the outer diameter of the overlapping portion as a whole.

Furthermore, in the embodiment, the first length L1 from the first end 30a of the second rigid portion 30 to the proximal end portion 42 of the flap 40 may be longer than the second length L2 from the proximal end portion 42 of the flap 40 to the boundary position Q. This is because an increase in the outer diameter of the portion in which the stent 1 is folded back may be suppressed by crushing the second rigid portion 30 even in such a configuration.

In the embodiment, the coil 22 is used as the first reinforcement portion. However, the first reinforcement portion is not limited thereto. For example, a blade 60 may be used as a first reinforcement portion as in a stent 2 shown in FIG. 8. As the blade 60, a known blade in which a metallic strand is woven in a mesh shape may be used.

For example, in the embodiment, the snare E20 is used to extract the stent to the outside of a body. However, the stent may be extracted by gripping the gripping target region R of the stent or hooking the proximal end portion 42 of the flap 40 using a gripping forceps instead of the snare E20. When the gripping forceps is used, it is desirable to select a gripping forceps in which a width of a gripping piece for gripping the stent 1 is sufficiently smaller than the second length L2.

In the embodiment, four flaps 40 are fixed to the proximal end side of the outer layer 24 of the stent 1. However, the number of the flaps 40 fixed to the outer layer 24 is not limited, and one to three flaps or five or more flaps may be provided. In the embodiment, an example has been described in which four flaps 40 are formed at equiangular intervals about the longitudinal axis C1, but these flaps 40 may not be formed at equiangular intervals about the longitudinal axis C1. The same also applies to the arrangement or the number of the flaps 50 fixed to the distal end side of the outer layer 24.

In the embodiment, an example has been described in which four flaps 50 are fixed to the outer layer 24 of the stent, but the stent may not include the flaps 50.

In the embodiment, the flap 40 is formed by notching and raising a portion. However, the flap 40 may be formed by fixing a member separate from the outer layer 24 to the outer layer 24 by thermal welding or the like. The same also applies to the flap 50.

In the embodiment, a case has been described in which the stent 1 is indwelled inside the bile duct P3. However, the stent 1 may be used while being indwelled inside a pancreas duct.

(Second Embodiment)

Hereinafter, a second embodiment of the stent according to the present invention will be described with reference to FIGS. 9 to 26. Furthermore, in all drawings below, the scales of the thicknesses and the dimensions of the components are appropriately changed in order for the drawings to be easily understood.

Figure 9:
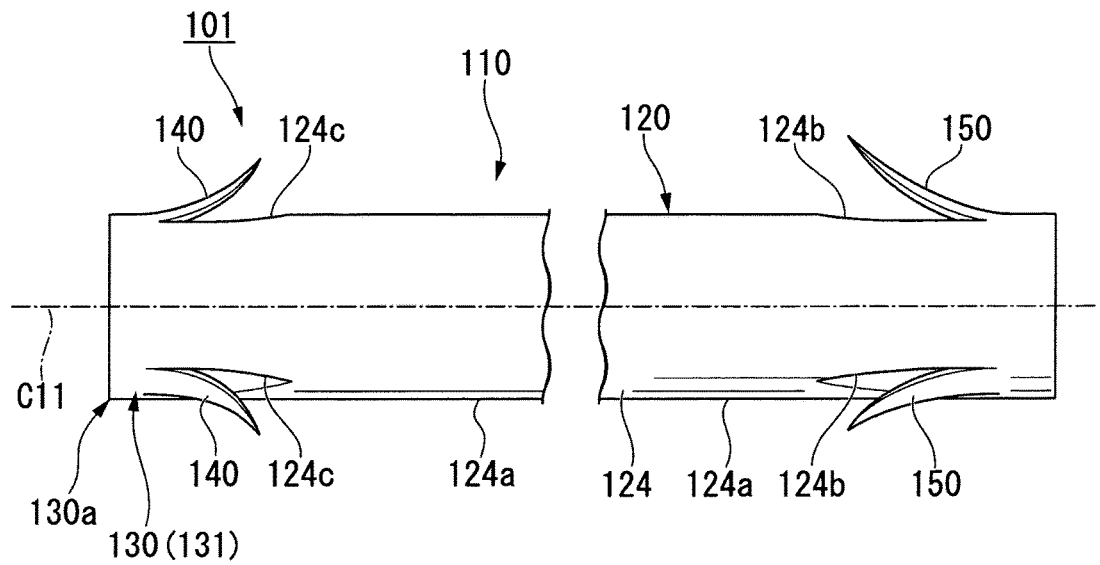
FIG. 9 is a side cross-sectional view showing a stent for medical use according to a second embodiment of the present invention.
Figure 10:
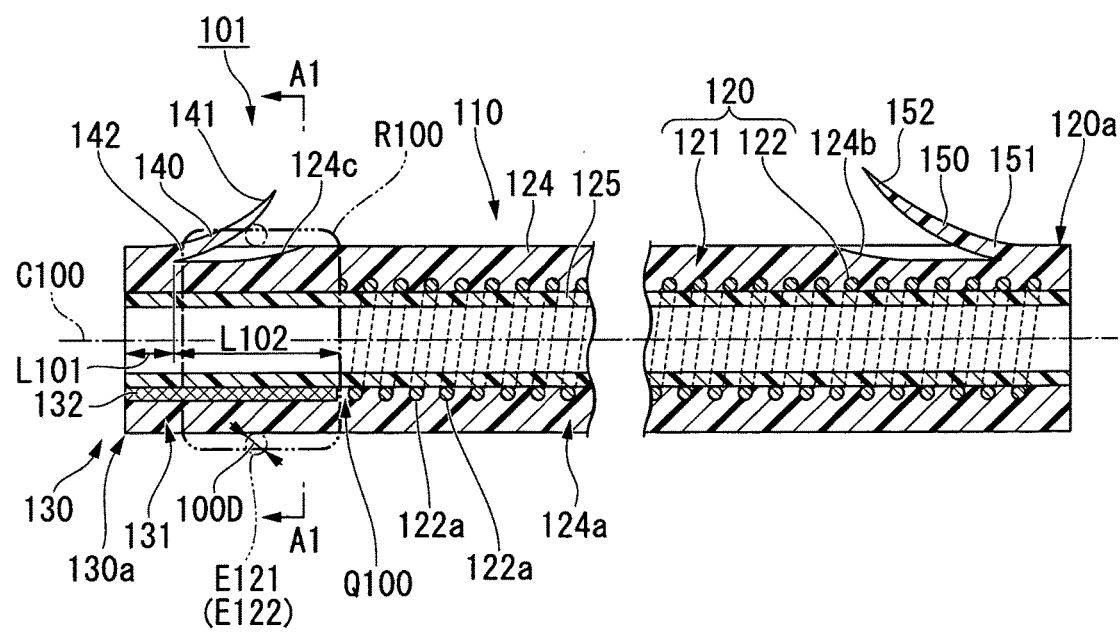
FIG. 10 is a side cross-sectional view showing the stent for medical use of the second embodiment of the present invention.

As shown in FIGS. 9 and 10, a stent 101 (a stent for medical use) according to the embodiment includes a main body 110 which includes a first rigid portion 120, a second rigid portion 130 and a flap (a locking member) 140. The main body 110 includes the first rigid portion 120 and the second rigid portion 130 which are formed in a tubular shape along a longitudinal axis C101. The flap 140 includes an extension portion 141 which extends outward in the radial direction of the main body 110 and a proximal end portion 142 which is connected to the extension portion 141 and is fixed to the second rigid portion 130.

The first rigid portion 120 includes a first resinous portion 121 and a coil (a first reinforcement portion) 122. The first resinous portion 121 is formed in a tubular shape. The coil 122 is firmly fixed to the first resinous portion 121. The first resinous portion 121 includes a distal end portion of an outer layer 124 which is formed in a tubular shape and a distal end portion of an inner layer 125 which is formed in a tubular shape and is formed at the inner circumferential side of the outer layer 124 to be coaxial with the outer layer 124. The outer layer 124 is formed of a resin material such as urethane or polyethylene having elasticity, flexibility, and biocompatibility. The outer layer 124 has, for example, an outer diameter of 3.2 mm (10 French) and a length of 100 mm. The outer layer 124 is formed not only at the outer circumferential surface side of the coil 122, but also at a gap between strands 122a, to be described later, of the coil 122.

In this example, three flaps 150 are formed at the end portion opposite to the second rigid portion 130 in the outer layer 124 that serves as a distal end side portion when the stent is inserted into a bile duct (one flap 150 is not shown). The flap 150 is formed by notching a part of the outer layer 124 and raising the notched portion. That is, the material of the flap 150 is the same as that of the outer layer 124. Three flaps 150 are formed at equiangular intervals about the longitudinal axis C101. Each flap 150 is formed so that a first end portion 151 is fixed to an outer circumferential surface of a second end portion 120a opposite to the second rigid portion 130 in the outer layer 124. The flap 150 is formed so that a second end portion 152 is opened outward in the radial direction of the main body 110 while extending along the longitudinal axis C101 toward a center portion 124a of the outer layer 124.

A notch portion 124b is formed in the outer circumferential surface of a position corresponding to each flap 150 in the outer layer 124. When the flap 150 is pressed from the outside of the radial direction toward the longitudinal axis C101, the flap 150 is received in the notch portion 124b.

The inner layer 125 is formed of, for example, a resin material such as PTFE (polytetrafluoroethylene) or PFA (perfluoroalkoxy alkane) having a smooth surface and biocompatibility. The inner layer 125 and the outer layer 124 are fixed to each other by thermal welding or the like.

The coil 122 is formed by winding the first strand (the strand) 122a about the longitudinal axis C101 in a spiral shape at the same pitch. The coil 122 is formed in a tubular shape as a whole by winding a first strand 122a once or more. The first strand 122a is formed of tungsten steel or stainless steel having a radiopaque property. The first strand 122a is formed of metal having an elastic modulus (tensile strength) greater than the outer layer 124 and the inner layer 125. The cross-section of the first strand 122a perpendicular to the longitudinal direction is formed in a circular shape. In the embodiment, the outer diameter of the first strand 122a is, for example, 0.11 mm. The pitch of the first strand 122a in the direction along the longitudinal axis C101 is, for example, about 0.41 mm (the gap between the first strands 122a is about 0.30 mm). The first strand 122a of the coil 122 is fixed (firmly fixed) to the outer layer 124 and the inner layer 125.

The coil 122 is provided at the boundary portion between the outer layer 124 and the inner layer 125 to be coaxial with the first resinous portion 121. That is, the coil 122 is provided at the inside of the first resinous portion 121 to be located at, for example, substantially the center in the radial direction. In the first rigid portion 120, the coil 122 is provided to maintain the tubular shape of the first resinous portion 121. The first rigid portion 120 has a predetermined rigidity with respect to a compression force in the radial direction. The rigidity mentioned herein mainly indicates the resisting force with respect to a force which crushes the stent in the radial direction.

Figure 11:
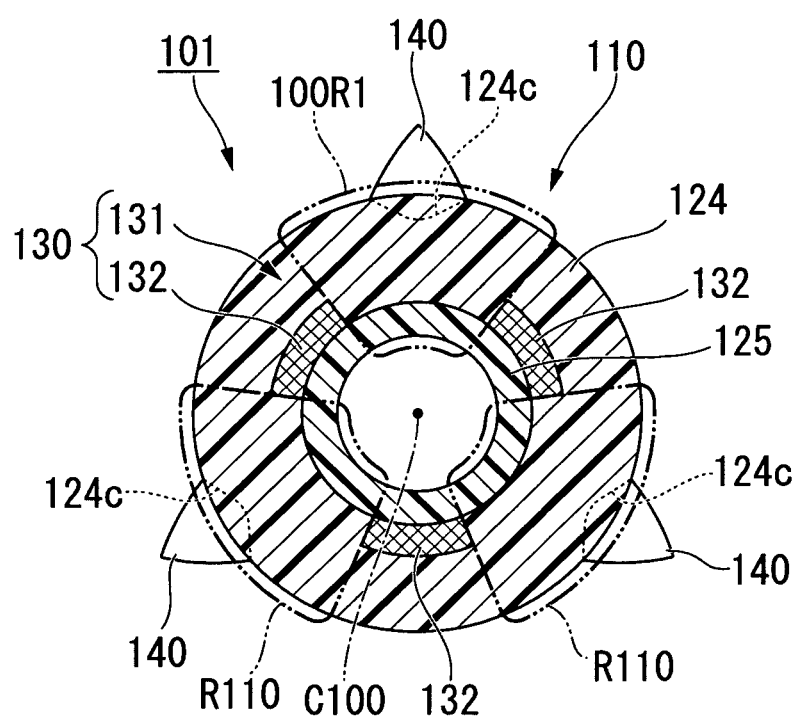
FIG. 11 is a cross-sectional view taken along a cut line A1-A1 of FIG. 10.

The second rigid portion 130 is formed in a tubular shape along the longitudinal axis C101. As shown in FIGS. 10 and 11, the second rigid portion 130 includes a second resinous portion 131 which is formed of a resin material in a tubular shape and a reinforcement plate (a second reinforcement portion) 132 which is fixed to the second resinous portion 131. The second resinous portion 131 includes a proximal end portion of the outer layer 124 and a proximal end portion of the inner layer 125. A wall portion of the second resinous portion 131 is formed by the proximal end portion of the outer layer 124 and the proximal end portion of the inner layer 125. The second resinous portion 131, that is, the second rigid portion 130 is connected to a proximal end portion of the first resinous portion 121 in a substantially coaxial state (also a coaxial state).

Three flaps 140 are formed at a first end 130a opposite to the first rigid portion 120 in the outer layer 124 that serves as a proximal end side portion when the stent is inserted into a bile duct (one flap 140 is not shown). Each flap 140 is formed by notching a part of the outer layer 124 and raising the notched portion. That is, the material of the flap 140 is the same as that of the outer layer 124. Three flaps 140 are formed at equiangular intervals about the longitudinal axis C101.

The flap 140 includes an extension portion 141 and a proximal end portion 142. In the flap 140, the proximal end portion 142 is fixed to an outer circumferential surface of the first end 130a opposite to the first rigid portion 120 in the second resinous portion 131. The flap 140 is formed so that the extension portion 141 is opened outward in the radial direction of the main body 110 while extending along the longitudinal axis C101 toward the center portion 124a of the outer layer 124. The proximal end portion 142 of the flap 140 is fixed to the second rigid portion 130 in the middle portion of the second rigid portion 130 in the direction along the longitudinal axis C101. The extension portion 141 is disposed at substantially the center position of the second rigid portion 130 in the direction along the longitudinal axis C101.

A first length L101 from the first end 130a opposite to the first rigid portion 120 in the second rigid portion 130 to the proximal end portion 142 of the flap 140 in the direction along the longitudinal axis C101 is, for example, 5 mm.

A notch portion 124c is formed in the outer circumferential surface at a position corresponding to each flap 140 of the outer layer 124. When the flap 140 is pressed from the outside of the radial direction toward the longitudinal axis C101, the flap 140 is received in the notch portion 124c.

The flap 140 is shorter than the flap 150. Since the flap 140 at the proximal end side (the duodenum side) is short, a smooth treatment may be performed by suppressing the flap 140 from being caught by a forceps raising base at an exit of an endoscope.

Here, as shown in FIG. 10, a boundary position Q100 is defined as a connection position between the first rigid portion 120 and the second rigid portion 130 in the direction along the longitudinal axis C101. The boundary position Q100 is a portion at which the end of the coil 122 at the proximal end side is located. The coil 122 is provided to be coaxial with the first resinous portion 121 in the range from the boundary position Q100 of the first resinous portion 121 to the end portion (the second end) 120a opposite to the second rigid portion 130 in the first rigid portion 120 in the direction along the longitudinal axis C101. In this example, a second length L102 from the proximal end portion 142 of the flap 140 to the boundary position Q100 is, for example, 7 mm.

The first length L101 is preferably short since the proximal end portion of the stent 101 protrudes from a duodenal papilla to a lumen of a duodenum when the stent is indwelled. However, when the flap 140 is fixed to the outer layer 124 by thermal welding or the like, it is desirable to ensure the first length L101 of 4 mm or more in order to also ensure fixing strength. The second length L102 is preferably set to be equal to or greater than 2 mm or equal to 8 mm.

A reinforcement plate 132 is formed in a plate shape extending in the direction along the longitudinal axis C101. The reinforcement plate 132 is formed of a material such as rigid urethane, nylon, and stainless steel having an elastic modulus greater than the outer layer 124 and the inner layer 125. As shown in FIG. 11, in the embodiment, the stent 101 is provided with three reinforcement plates 132. The reinforcement plates 132 are provided at a position not overlapping the flaps 140 in the circumferential direction of the main body 110 at equiangular intervals about the longitudinal axis C101 when viewed in the direction along the longitudinal axis C101. That is, the reinforcement plate 132 is fixed so that the reinforcement plate is not disposed between the flap 140 and the longitudinal axis C101 in the radial direction of the stent 101. The reinforcement plates 132 are provided at an interval in the circumferential direction about the longitudinal axis C101 of the second resinous portion 131.

In this way, the reinforcement plate 132 is not provided in a region R101 in a part of the second resinous portion 131 in the circumferential direction, and is provided in a remaining portion other than the region R101 in the second resinous portion 131 in the circumferential direction. The outer layer 124 is provided between the adjacent reinforcement plates 132 in the circumferential direction.

As shown in FIG. 10, each reinforcement plate 132 is provided in the range from the first end 130a of the second rigid portion 130 which is positioned opposite to the first rigid portion 120 to the boundary position Q100 in the direction along the longitudinal axis C101. In this example, at least one of three reinforcement plates 132 is connected to the coil 122 by bonding or welding. The rigidity of the second rigid portion 130 is less than that of the first rigid portion 120, such that the outer layer 124 between the adjacent reinforcement plates 132 in the circumferential direction is compressed or extruded from the adjacent reinforcement plates 132 when the stent 101 is crushed in the radial direction of the main body 110. That is, the second rigid portion 130 is formed to be easily crushed in the radial direction compared to the first rigid portion 120. In the description below, the range from the center portion 124a of the proximal end portion 142 of the flap 140 in the second rigid portion 130 to the boundary position Q100 is indicated by a gripping target region R100.

Next, the action of the stent 101 with the above-described configuration will be described below by exemplifying an operation in which the stent 101 is indwelled in a bile duct and the indwelled stent 101 is replaced.

Figure 12:
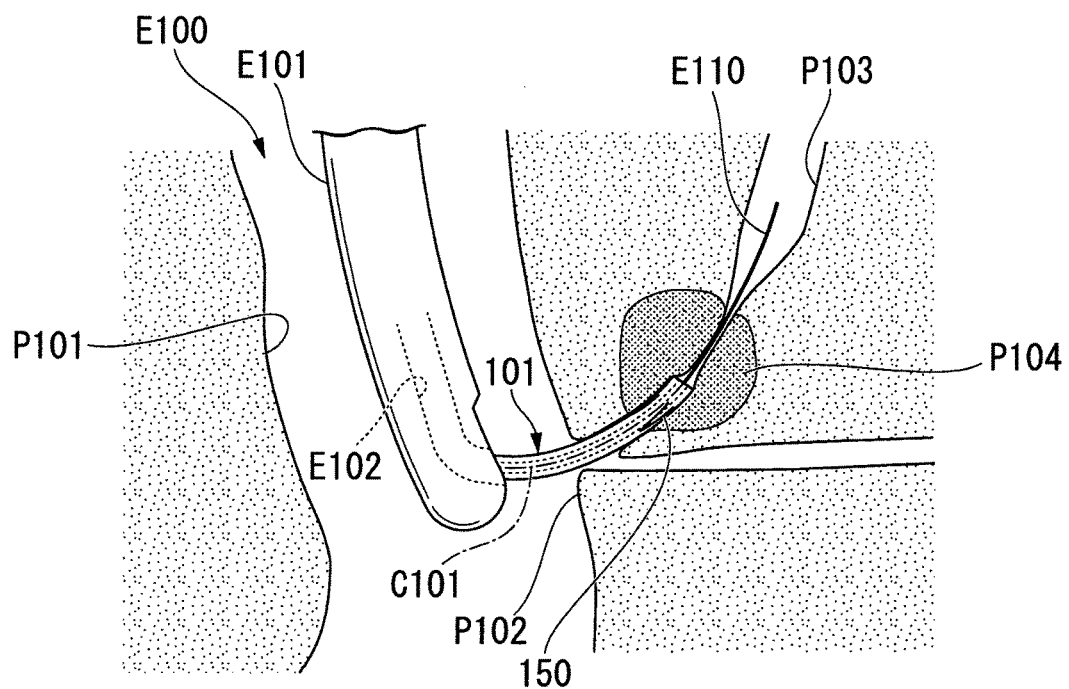
FIG. 12 is a view showing a procedure of indwelling the stent for medical use according to the second embodiment of the present invention.

First, a user such as an operator inserts a lateral vision type endoscope from a natural opening such as a mouth into a patient's body cavity, and inserts a distal end of an insertion portion E101 of an endoscope E in the vicinity of a duodenal papilla (a tissue) P102 through a duodenum P101 as shown in FIG. 12.

Next, the user inserts a guide wire E110 from a forceps opening (not shown) of an endoscope E100 into a channel E102, and causes a distal end of the guide wire E110 to protrude from a distal end opening of the channel E102 toward the duodenal papilla P102 while appropriately operating a raising table (not shown). Then, the distal end of the guide wire E110 is inserted from the duodenal papilla P102 into a bile duct P103.

Next, the user checks the shapes of a narrowed area P104 of the bile duct P103 and the duodenal papilla P102 using fluoroscopy, and selects the stent 101 having a proper length. That is, the stent 101 in which the length from the extension portion 141 of the flap 140 to the second end portion 152 of the flap 150 is longer than the length from the duodenal papilla P102 to the narrowed area P104 of the bile duct P103 when the flaps 140 and 150 are opened is selected.

Next, the user inserts the stent 101 into the bile duct P103 from the flap 150 along the guide wire E110 by a stent delivery catheter (not shown) inserted from the forceps opening while checking the positions and the shapes of the stent 101 and the bile duct P103.

Figure 13:
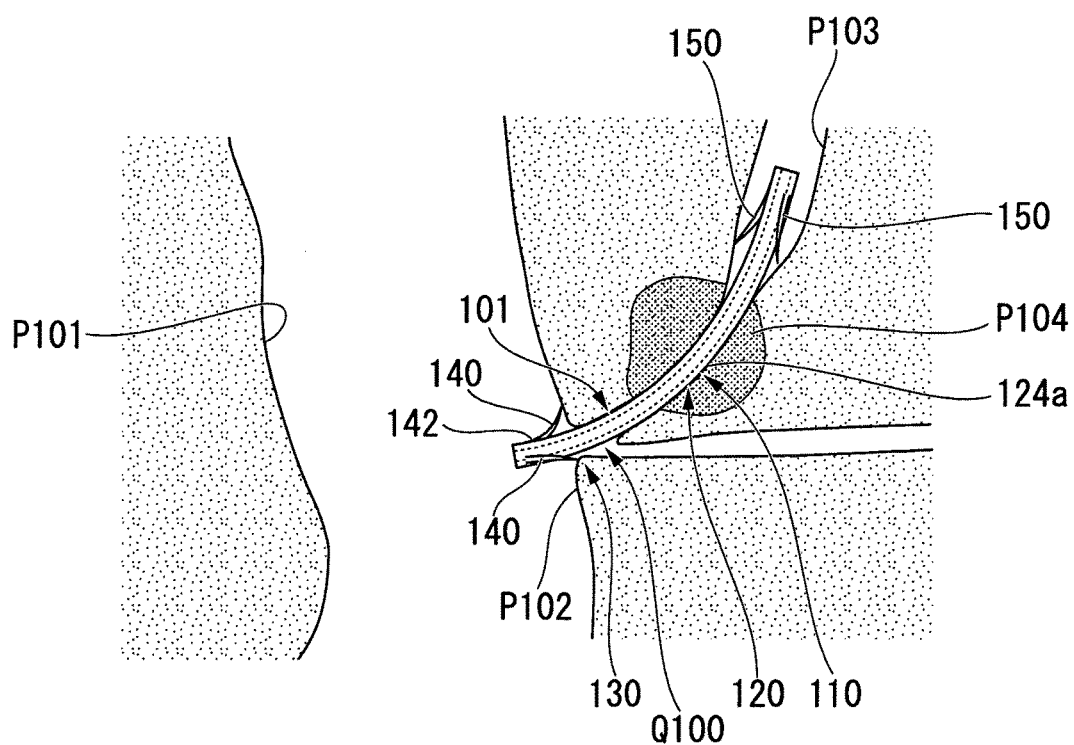
FIG. 13 is a view showing a procedure of indwelling the stent for medical use according to the second embodiment of the present invention.

When a distal end of the stent 101 reaches the narrowed area P104 of the bile duct P103, the flap 150 is pressed toward the longitudinal axis C101 by the narrowed area P104, and the flap 150 is received in the notch portion 124b. When the stent 101 is further inserted into the bile duct P103 and the flap 150 advances beyond the narrowed area P104, the second end portion 152 of the flap 150 is opened and the flap 150 is locked to the narrowed area P104 as shown in FIG. 13.

At this time, since the stent 101 in which the length from the extension portion 141 of the flap 140 to the second end portion 152 of the flap 150 is set to the above-described length is selected, the flap 140 is also locked to the duodenal papilla P102. Accordingly, at least a proximal end portion of the second rigid portion 130 protrudes from the duodenal papilla P102 into a lumen of the duodenum P101 to be indwelled therein. In other words, an outer circumferential surface of the main body 110 which is slightly close to the center portion 124a in relation to the proximal end portion 142 of the flap 140 protrudes into the lumen of the duodenum P101 in the indwelled state. Meanwhile, the first rigid portion 120 is indwelled inside the bile duct P103.

The boundary position Q100 of the stent 101 is located in the vicinity of the duodenal papilla P102. That is, the second rigid portion 130 is located substantially inside the duodenum P101. Thus, a space inside a tube conduit of a portion which is pressed by the bile duct P103 or the like in the stent 101 is maintained by the coil 122.

Next, the user extracts the guide wire E110 and the insertion portion E101 of the endoscope E100 from the patient's body cavity, and ends the operation of indwelling the stent 101. Next, when the stent 101 is indwelled for a predetermined period of time, the indwelled stent 101 is replaced by a new stent 101, as will be described later.

Figure 14:
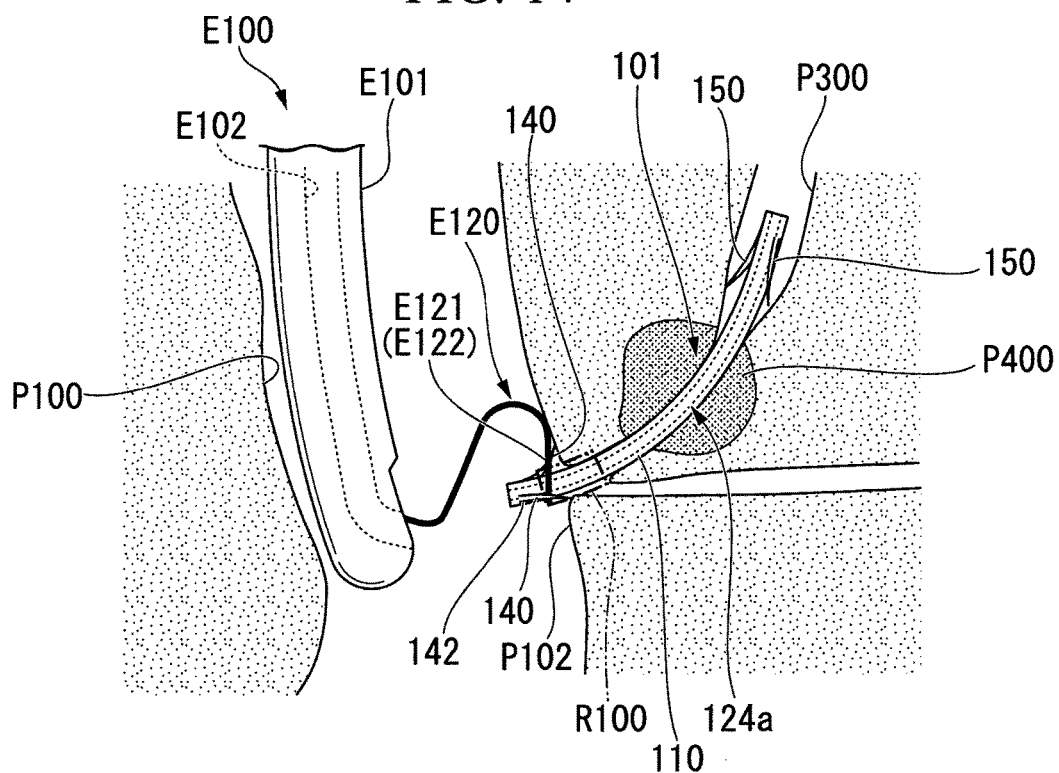
FIG. 14 is a view showing a procedure of replacing the indwelled stent for medical use of the second embodiment of the present invention.

First, as described above, the user inserts a distal end of the insertion portion E101 of the endoscope E100 into the vicinity of the duodenal papilla P102 through the duodenum P101 as shown in FIG. 14.

A snare E120 is inserted into the channel E102 through the forceps opening. A loop portion E121 of the snare E120 is obtained by forming a wire E122 in a loop shape. The snare E120 is pressed into the forceps opening, and the loop portion E121 is caused to protrude from the distal end opening of the channel E102. The loop portion E121 is hooked to the gripping target region 8100 of the stent 101 through the proximal end of the stent 101 in the loop portion E121. More specifically, the loop portion E121 is hooked to the outer circumferential surface of the main body 110 which is slightly close to the center portion 124a in relation to the proximal end portion 142 of the flap 140.

When the snare E120 is pulled back while the position of the insertion portion E101 is fixed, the loop portion E121 is hooked to the center portion 124a of the proximal end portion 142 of the flap 140 in the main body 110 as shown in FIGS. 10 and 14.

Figure 15:
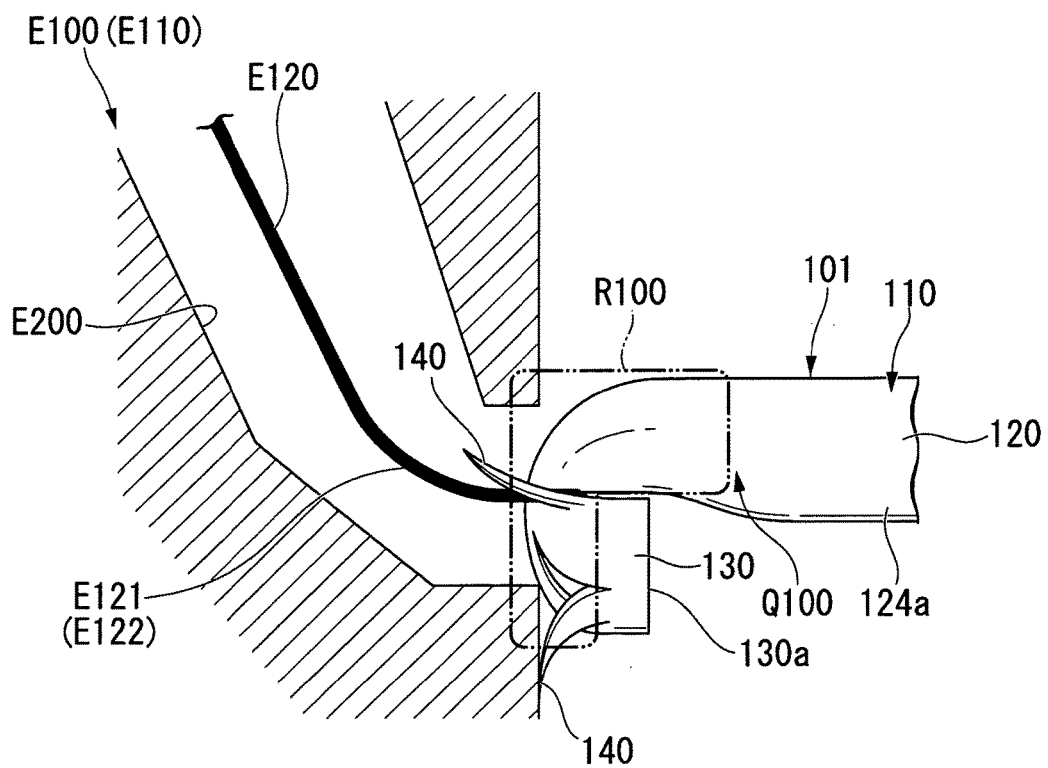
FIG. 15 is a view showing a procedure of replacing the indwelled stent for medical use of the second embodiment of the present invention.
Figure 16:
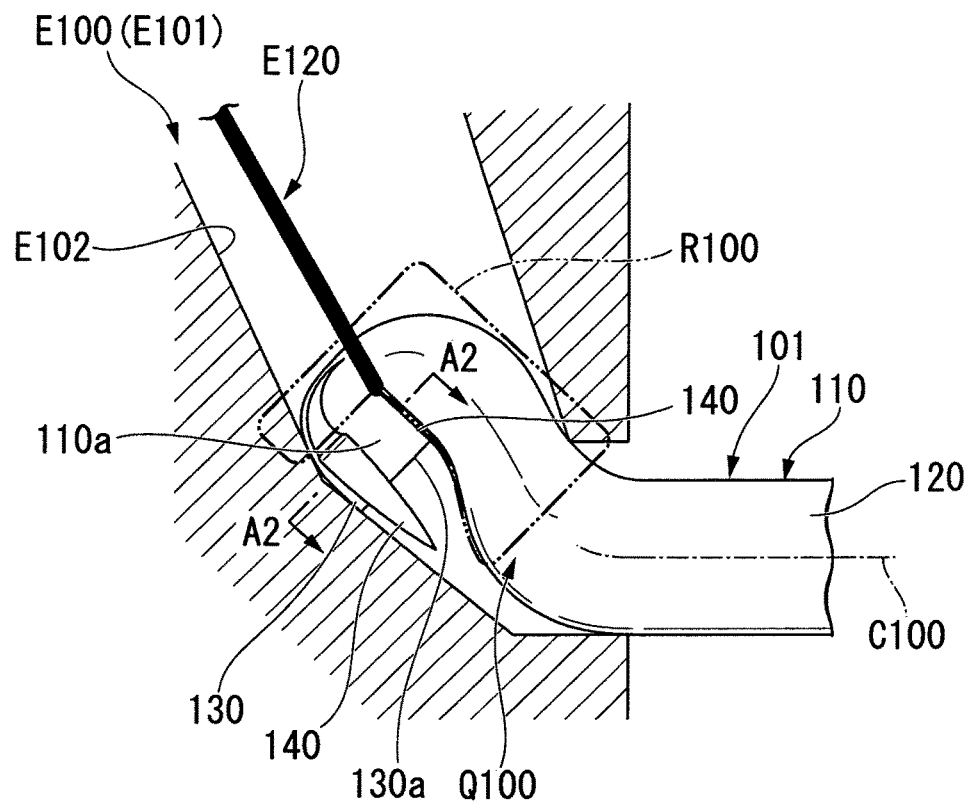
FIG. 16 is a view showing a procedure of replacing the indwelled stent for medical use of the second embodiment of the present invention.
Figure 17:
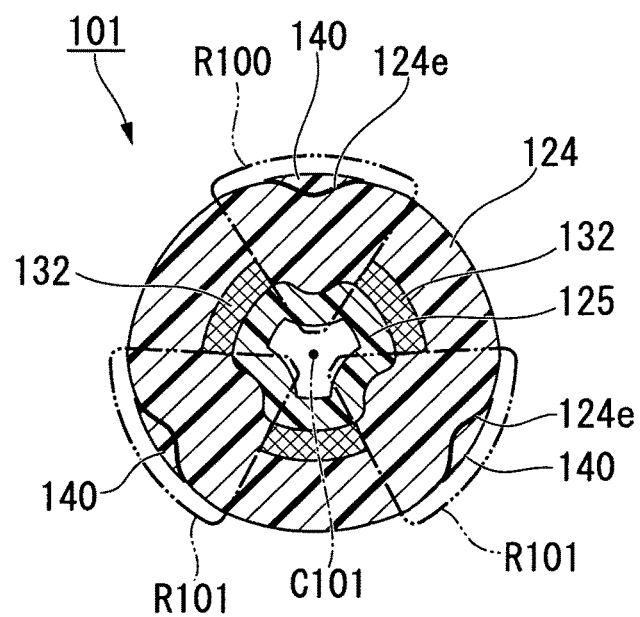
FIG. 17 is a cross-sectional view taken along a cut line A2-A2 of FIG. 16.

When the snare E120 is pulled back, the stent 101 is extracted from the bile duct P103, and the stent 101 is led into the channel E102 of the insertion portion E101 as shown in FIG. 15. At this time, the held gripping target region R100 of the stent 101 first enters the channel E102, and a distal end side portion in relation to the gripping target region R100 in the stent 101 and the first end 130a of the second rigid portion 130, which is a proximal end side portion, subsequently enter the channel E102. That is, the stent 101 is led into the channel E102 while being folded back at the gripping target region R100. Since the outer diameter of the stent 101 increases as a whole in a portion in which the stent 101 is folded back, the stent 101 is crushed in the radial direction when the stent is led into the channel E102 as shown in FIGS. 16 and 17. When the stent is led into the channel E102, there is a case in which the flap 140 is folded back toward the first end 130a of the second rigid portion 130.

Since the region R101 of the second rigid portion 130 is easily compressed in the circumferential direction compared to the first rigid portion 120, the second rigid portion 130 may be easily crushed in the radial direction. The region R101 in which the reinforcement plate 132 is not provided in the circumferential direction is easily crushed in the radial direction compared to the region provided with the reinforcement plate 132. A recess 124e which is recessed toward the longitudinal axis C101 is formed in the outer circumferential surface of the outer layer 124 at the region R101. When the stent is led into the channel E102 and the flap 140 is folded back, the folded-back flap 140 is received in the recess 124e.

When the stent is led into the channel E102, the second rigid portion 130 of the stent 101 is pulled in the direction along the longitudinal axis C101. The second rigid portion 130 is provided with the reinforcement plate 132 which is formed of a material having an elastic modulus greater than the outer layer 124 and the inner layer 125. For this reason, the rigidity of the second rigid portion 130 in the direction along the longitudinal axis C101 is greater. Further, since at least one of three reinforcement plates 132 is connected to the coil 122, the rigidity of the connection portion between the second rigid portion 130 and the first rigid portion 120 is also great. Since the stent 101 has such a configuration, it is possible to suppress the second rigid portion 130 from being torn in the direction along the longitudinal axis C101 when the stent is led into the channel E102.

When the portion in which the stent 101 is folded back in the overlapping state passes through the channel E102, the remaining portions of the stent 101 also pass through the channel E102 together.

In this way, the snare E120 is pulled back while the position of the insertion portion E101 is fixed, and the stent 101 and the snare E120 are extracted to the outside of a body through the channel E102. Subsequently, the guide wire E110 is inserted into the channel E102 and a new stent 101 is indwelled inside the bile duct P103 through the channel E102 as described above.

According to the stent 101 of the embodiment, since the rigidity of the first rigid portion 120 is greater than that of the second rigid portion 130, a space inside a tube conduit of a portion which is pressed by the bile duct P103 or the like in the indwelled state is maintained. Since the rigidity of the second rigid portion 130 is less than that of the first rigid portion 120, the gripping target region R100 which is a part of the second rigid portion 130 and is a portion first led into the channel E102 is easily crushed, that is, deformed, in the radial direction compared to the first rigid portion 120 when the stent 101 passes through the channel E102 for the stent to be collected.

Since the second rigid portion 130 is provided with the reinforcement plate 132, the rigidity in the direction along the longitudinal axis C101 increases, the second rigid portion 130 may not be easily broken when the second rigid portion is pulled in the direction along the longitudinal axis C101.

Each reinforcement plate 132 is provided at a position not overlapping the flap 140 in the circumferential direction of the main body 110 when viewed in the direction along the longitudinal axis C101. When the snare E120 in which the loop portion E121 is locked to the gripping target region R100 is pulled back, the recess 124e is formed in the outer circumferential surface of the outer layer 124 at the region R101. Since the folded-back flap 140 is received in the recess 124e, it is possible to suppress an increase in the outer diameter of the folded-back stent 101 as a whole.

Since the reinforcement plate 132 is formed in a plate shape extending in the direction along the longitudinal axis C101, the configuration of the reinforcement plate 132 becomes simple, and hence the reinforcement plate 132 may be easily formed.

Since the reinforcement plate 132 is connected to the coil 122, the stent 101 may have great rigidity at the boundary position Q100.

In the embodiment, three flaps 140 are formed in the outer layer 124 of the stent 101, and three reinforcement plates 132 are provided in the second rigid portion 130. However, the number of the flaps 140 and the reinforcement plates 132 is not limited. For example, the outer layer 124 may be provided with one or more flaps 140 and the second rigid portion 130 may be provided with one or more reinforcement plates 132. In the embodiment, three flaps 140 are formed at equiangular intervals about the longitudinal axis C101, but these flaps 140 may not be formed at equiangular intervals about the longitudinal axis C101. The same also applies to the arrangement or the number of the flaps 150 formed in the outer layer 124.

In the embodiment, each reinforcement plate 132 is provided in the range from the end portion of the second rigid portion 130 which is positioned opposite to the first rigid portion 120 to the boundary position Q100 in the direction along the longitudinal axis C101. However, the reinforcement plate 132 may be provided in at least the gripping target region R100. Even in such a configuration, the stent 101 may have great rigidity at a portion to which the wire E122 of the snare E120 is locked.

In the embodiment, at least one of three reinforcement plates 132 is connected to the coil 122, but no reinforcement plates 132 need be connected to the coil 122. In this case, the rigidity of the stent 101 at the boundary position Q100 decreases.

As the snare E120 used to replace the stent 101, a snare in which the outer diameter D (see FIG. 10) of the wire E122 forming the loop portion E121 is sufficiently smaller than the second length L102 is used. Since such a snare E120 is used, the wire E122 is apart from the boundary position Q100 in the direction along the longitudinal axis C101 when the loop portion E121 is locked to the gripping target region R. When an excessive force is exerted on the boundary position Q100 of the stent 101 having little rigidity, the stent may be broken at the boundary position Q100. However, since the snare E120 is selected as described above, the stent 101 may not be easily broken at the boundary position Q100 when no reinforcement plates 132 are connected to the coil 122.

(Third Embodiment)

Next, a third embodiment according to the present invention will be described with reference to FIGS. 18 to 22, but only the differences from the above-described embodiments will be described by giving the same reference numerals to the same components as the above-described embodiments and omitting a repetitive description thereof.

Figure 18:
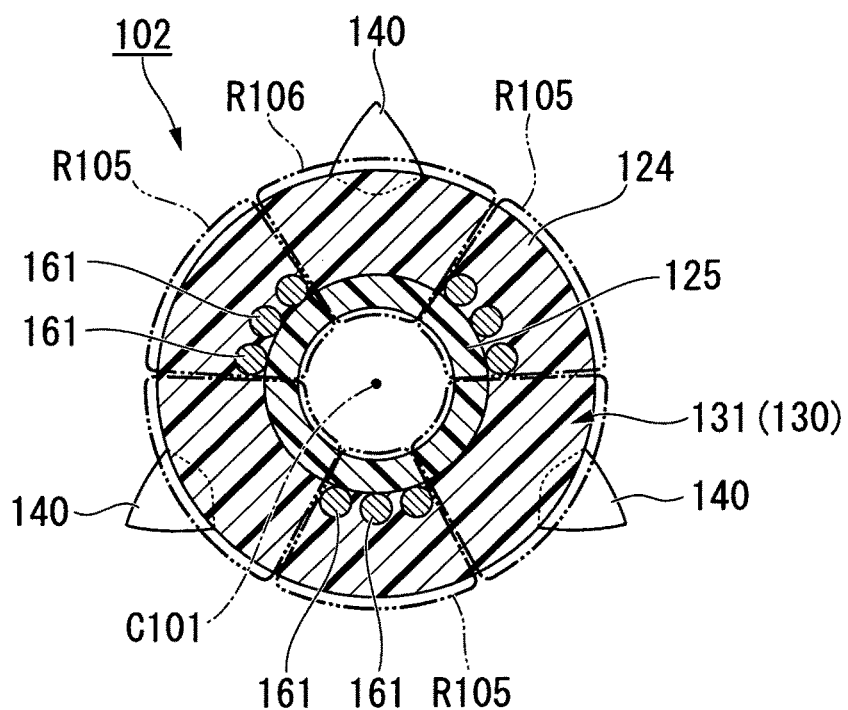
FIG. 18 is a front cross-sectional view showing a stent for medical use according to a third embodiment of the present invention.

As shown in FIG. 18, a stent 102 (a stent for medical use) according to the embodiment includes a plurality of bar-shaped bodies (second reinforcement portions) 161 instead of the reinforcement plate 132 of the stent 101 according to the second embodiment.

Each bar-shaped body 161 is formed in a columnar shape (a bar shape) extending in the direction along the longitudinal axis C101. The bar-shaped body 161 may be formed of the same material as the reinforcement plate 132. Each bar-shaped body 161 is provided in a region R105 of a position not overlapping the flap 140 in the circumferential direction of the second resinous portion 131 when viewed in the direction along the longitudinal axis C101. That is, the bar-shaped body 161 is not disposed between the flap 140 and the longitudinal axis C101.

Figure 19:
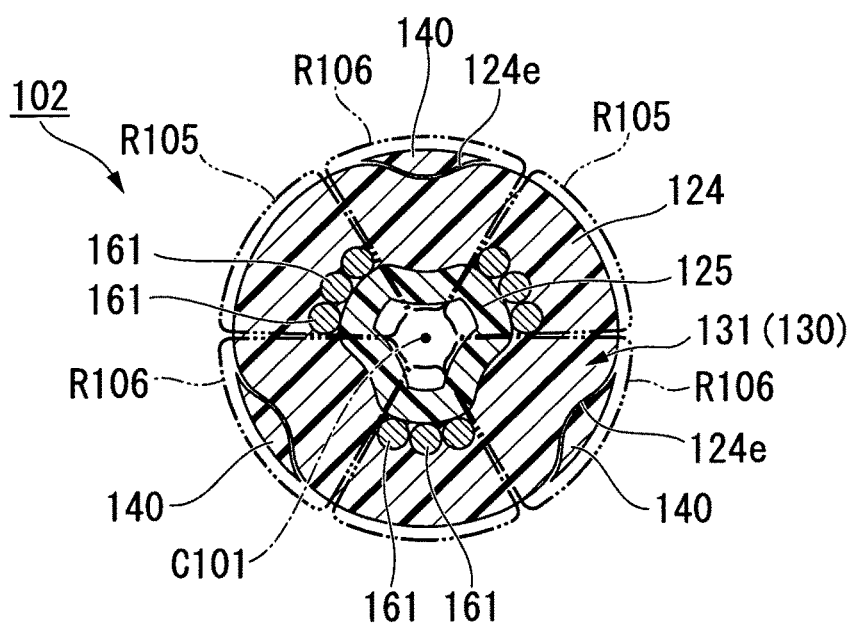
FIG. 19 is a front cross-sectional view showing a state in which the stent for medical use according to the third embodiment of the present invention is crushed.

Three bar-shaped bodies 161 are provided at an interval in the circumferential direction in the region R105 between the adjacent flaps 140 in the circumferential direction. The outer layer 124 is provided between the adjacent bar-shaped bodies 161 in the circumferential direction. The stent 102 with such a configuration becomes as shown in FIG. 19 when the loop portion E121 is locked to the gripping target region R100 and the snare E120 is pulled back. That is, a region R106 of the second resinous portion 131 without the bar-shaped body 161 in the circumferential direction is easily crushed in the radial direction compared to the region R105 with the bar-shaped body 161, and the recess 124e is formed in the outer circumferential surface of the outer layer 124 at the region R106.

As the stent 102 is crushed, the outer layer 124 between the adjacent bar-shaped bodies 161 in the circumferential direction in each region R105 is compressed and is extruded from the gap between the bar-shaped bodies 161.

The stent 102 of the embodiment may maintain a space inside a tube conduit in the indwelled state. Further, the stent is easily crushed, that is, deformed, and is not easily broken during the extraction operation.

Since the bar-shaped body 161 is formed in a columnar shape extending in the direction along the longitudinal axis C101, the configuration of the bar-shaped body 161 becomes simple, and hence the bar-shaped body 161 may be easily formed.

Since three bar-shaped bodies 161 are provided at an interval in the circumferential direction in each region R105, three bar-shaped bodies 161 are easily crushed in the circumferential direction as a whole. Thus, the second rigid portion 130 of the stent 102 may be more simply crushed.

Furthermore, in the embodiment, three bar-shaped bodies 161 are formed in each region R105. However, the number of the bar-shaped bodies 161 provided in the region R105 is not limited, and two or four or more bar-shaped bodies may be provided as long as a plurality of bar-shaped bodies are provided.

Figure 20:
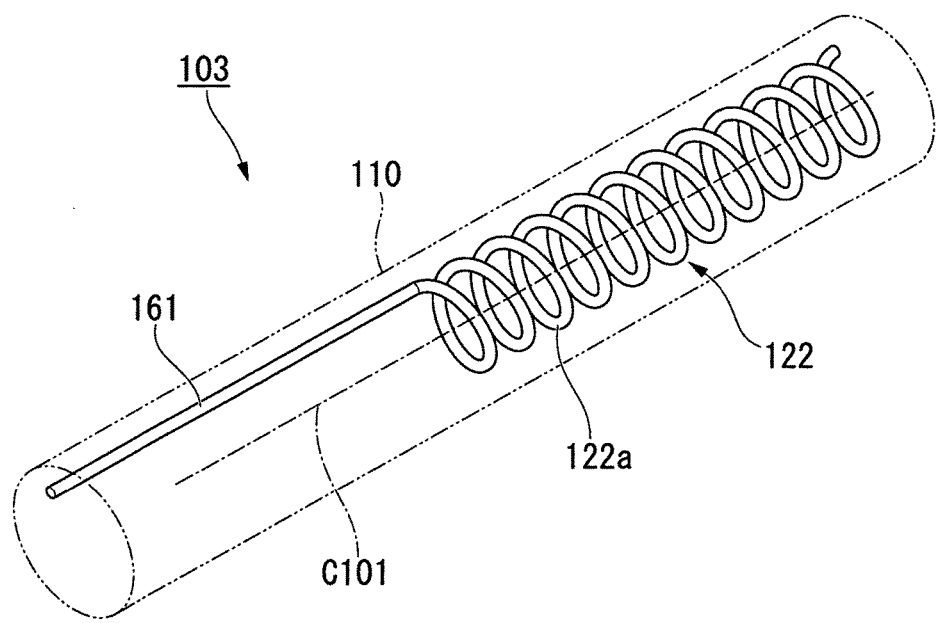
FIG. 20 is a perspective view transparently showing a stent for medical use according to a modified example of the third embodiment of the present invention.

The configuration of the stent 102 according to the embodiment may be modified in various ways as will be described below. For example, only one bar-shaped body 161 may be provided as in a stent 103 (a stent for medical use) of a modified example shown in FIG. 20. In FIG. 20, the flaps 140 and 150 are not shown. The bar-shaped body 161 extends in the direction along the longitudinal axis C101 and is connected to the coil 122. In this case, the coil 122 and the bar-shaped body 161 may be integrally formed by bending one strand, and hence the stent 103 may be easily manufactured.

Figure 21:
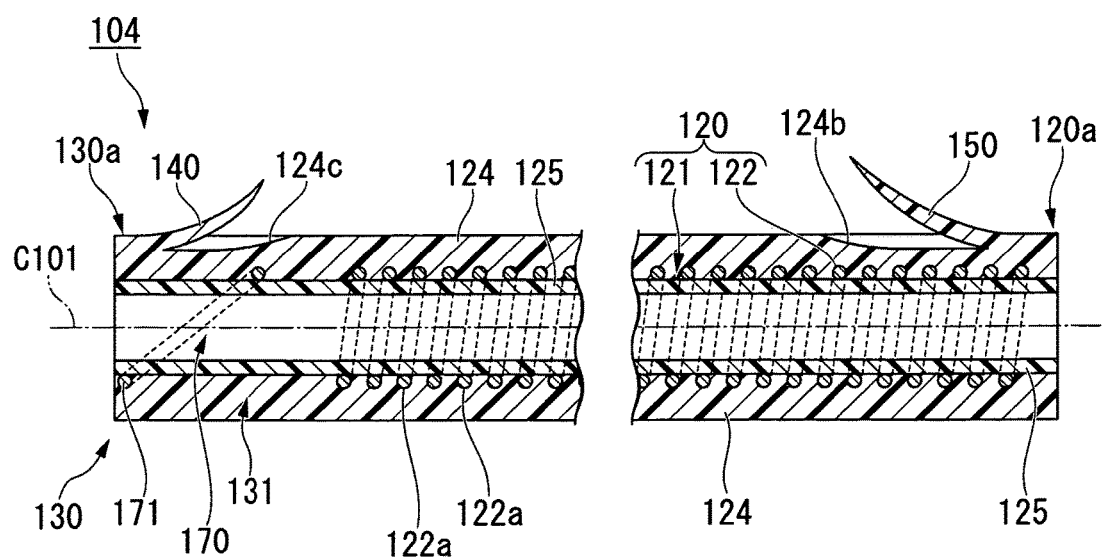
FIG. 21 is a side cross-sectional view showing the stent for medical use of the modified example of the third embodiment of the present invention.

As in a stent 104 (a stent for medical use) of a modified example shown in FIG. 21, a second reinforcement portion 170 may be formed in a shape in which a second strand 171 is wound in a spiral shape about the longitudinal axis C101. The second reinforcement portion 170 is coaxial with the second resinous portion 131, and is provided between the outer layer 124 and the inner layer 125, that is, the middle portion of the second resinous portion 131 in the radial direction.

Figure 22:
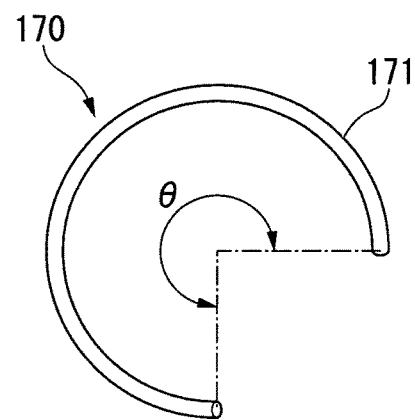
FIG. 22 is a front view showing a second reinforcement portion of the stent for medical use of the modified example of the third embodiment of the present invention.

As shown in FIG. 22, the center angle θ of the second reinforcement portion 170 when viewed in the direction along the longitudinal axis C101 is an angle smaller than 360°. For example, the center angle is 270°. The coil 122 and the second reinforcement portion 170 are integrally formed with each other by bending one strand. Since the second reinforcement portion 170 is formed in this way, a region without the second reinforcement portion 170 in the circumferential direction is formed when the second rigid portion 130 is viewed in the direction along the longitudinal axis C101, and hence the second rigid portion 130 is easily crushed. The stent 104 with such a configuration may be easily manufactured by integrally forming the coil 122 and the second reinforcement portion 170.

Furthermore, the stent 103 of the modified example may be formed by forming the coil 122 and the bar-shaped body 161 integrally with each other such as by welding the coil 122 and the bar-shaped body 161 which are separately formed by the strand. The same also applies to the stent 104 of the modified example.

(Fourth Embodiment)

Next, a fourth embodiment of the present invention will be described with reference to FIG. 23, but only the differences from the above-described embodiments will be described by giving the same reference numerals to the same components as the above-described embodiments and omitting a repetitive description thereof.

Figure 23:
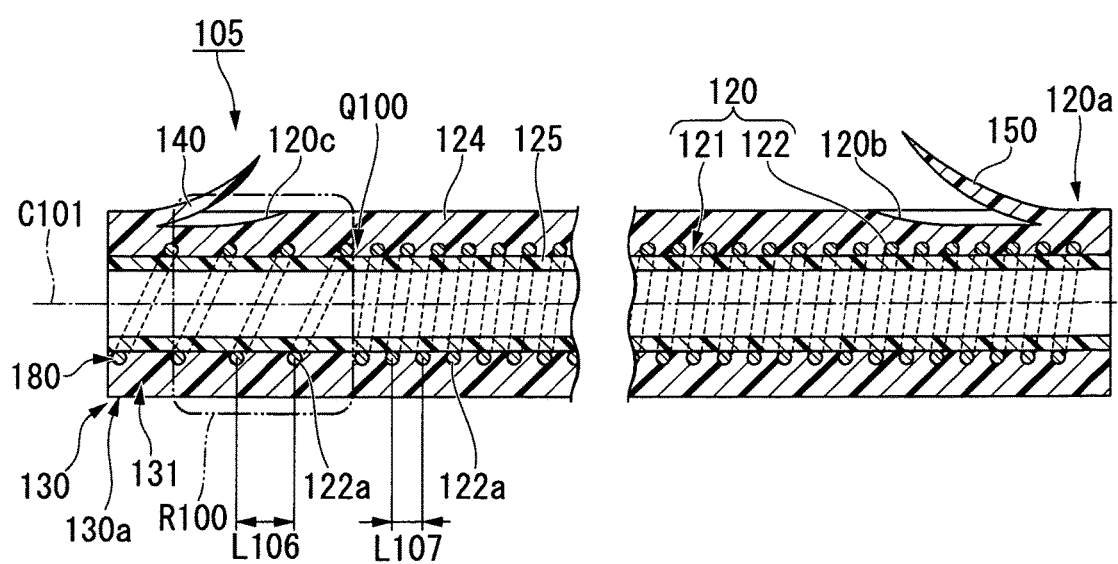
FIG. 23 is a side cross-sectional view showing a stent for medical use according to a fourth embodiment of the present invention.

As shown in FIG. 23, a stent 105 (a stent for medical use) according to the embodiment includes a coil (a second reinforcement portion) 180 instead of three reinforcement plates 132 of the stent 101 according to the second embodiment.

A coil 180 is formed by winding the first strand 122a in a spiral shape at the same pitch about the longitudinal axis C101. The coil 180 is formed in a tubular shape as a whole by winding the first strand 122a once or more. The coil 180 and the coil 122 are integrally formed with each other by the same first strand 122a, and are formed in a tubular shape as a whole.

The coil 180 is provided at the boundary portion between the outer layer 124 and the inner layer 125 to be coaxial with the second resinous portion 131. The first strand 122a of the coil 180 is fixed (firmly fixed) to the outer layer 124 and the inner layer 125. The coil 180 is provided to maintain the tubular shape of the second resinous portion 131.

The coil 180 and the coil 122 have the same outer diameter. A pitch L106 of the first strand 122a in the coil 180 is larger than a pitch L107 of the first strand 122a in the coil 122. The rigidity of the coil 180 is less than that of the coil 122 because the first strand 122a with the large pitch L106 is used. It is more desirable that the pitch L106 of the coil 180 be equal to or greater than 1.1 times and equal to or less than 5 times the pitch L107 of the coil 122.

In the stent 105 according to the embodiment with such a configuration, a space inside a tube conduit in the indwelled state is mainly held by the coil 122.

When the stent 105 is extracted, the loop portion E121 is locked to the gripping target region R100. Since the rigidity of the coil 180 is less than that of the coil 122, the stent 105 is formed so that the second rigid portion 130 is easily crushed in the radial direction compared to the first rigid portion 120.

According to the stent 105 of the embodiment, the stent may maintain a space inside a tube conduit in the indwelled state. Further, the stent may be easily crushed, that is, deformed, during the extraction operation.

Since the rigidity of the coil 180 is less than that of the coil 122, the gripping target region R100 in a part of the second rigid portion 130 may be easily crushed, that is, deformed, in the radial direction compared to the first rigid portion 120.

In the embodiment, the rigidity of the coil 180 may be set to be less than that of the coil 122 by setting the outer diameter of the strand forming the coil 180 to be smaller than that of the strand forming the coil 122. Further, the rigidity of the coil 180 may be set to be less than that of the coil 122 by which both the outer diameter of the strands forming the coil 122 and of the coil 180 and outer diameter of a whole of the coils 122 and 180 are set to be equal to each other while the elastic modulus of the strand forming the coil 180 to be less than that of the strand forming the coil 122.

(Fifth Embodiment)

Next, a fifth embodiment of the present invention will be described with reference to FIGS. 24 and 25, but only the differences from the above-described embodiments will be described by giving the same reference numerals to the same components as the above-described embodiments and omitting the repetitive description thereof.

Figure 24:
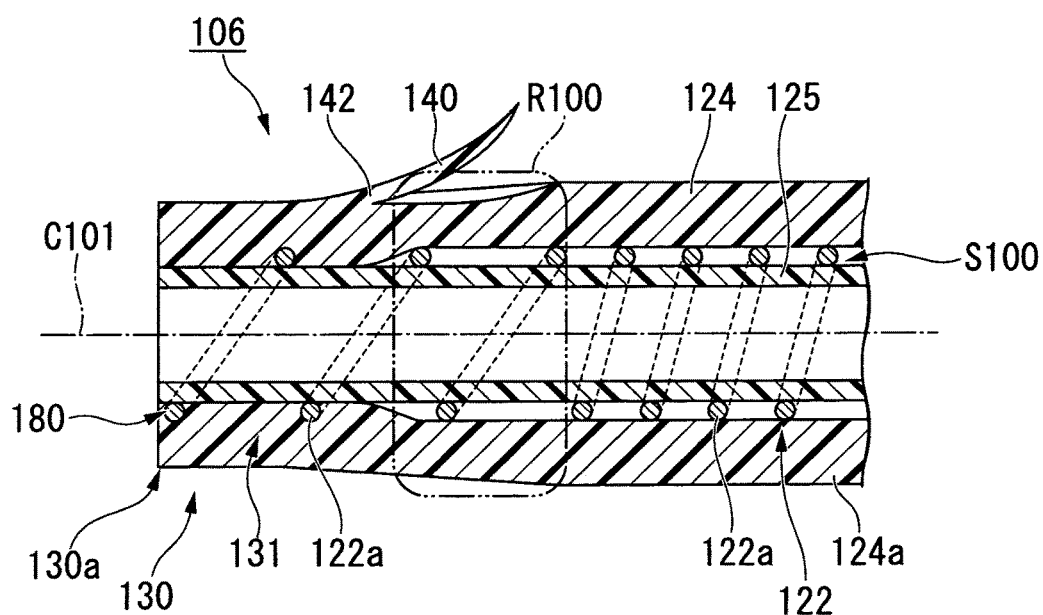
FIG. 24 is a cross-sectional view showing a major part of a stent for medical use according to a fifth embodiment of the present invention.

As shown in FIG. 24, a stent 106 (a stent for medical use) according to the embodiment has a configuration in which a gap S100 is formed at the boundary portion between the outer layer 124 and the inner layer 125 in the configuration of the stent 105 according to the fourth embodiment so that the gap is formed in the range from the proximal end portion 142 of the flap 140 to the center portion 124a of the outer layer 124 in the direction along the longitudinal axis C101. The first strand 122a is disposed inside the gap S100. The first strand 122a is formed to be movable in the direction along the longitudinal axis C101 with respect to the outer layer 124 and the inner layer 125. The first strand 122a, which is disposed at a position other than the gap S100, is fixed to the outer layer 124 and the inner layer 125.

The gap S100 is formed by thermally welding the range other than the gap S100 without thermally welding the outer layer 124 and the inner layer 125 in the range corresponding to the gap S100 in the direction along the longitudinal axis C101.

Figure 25:
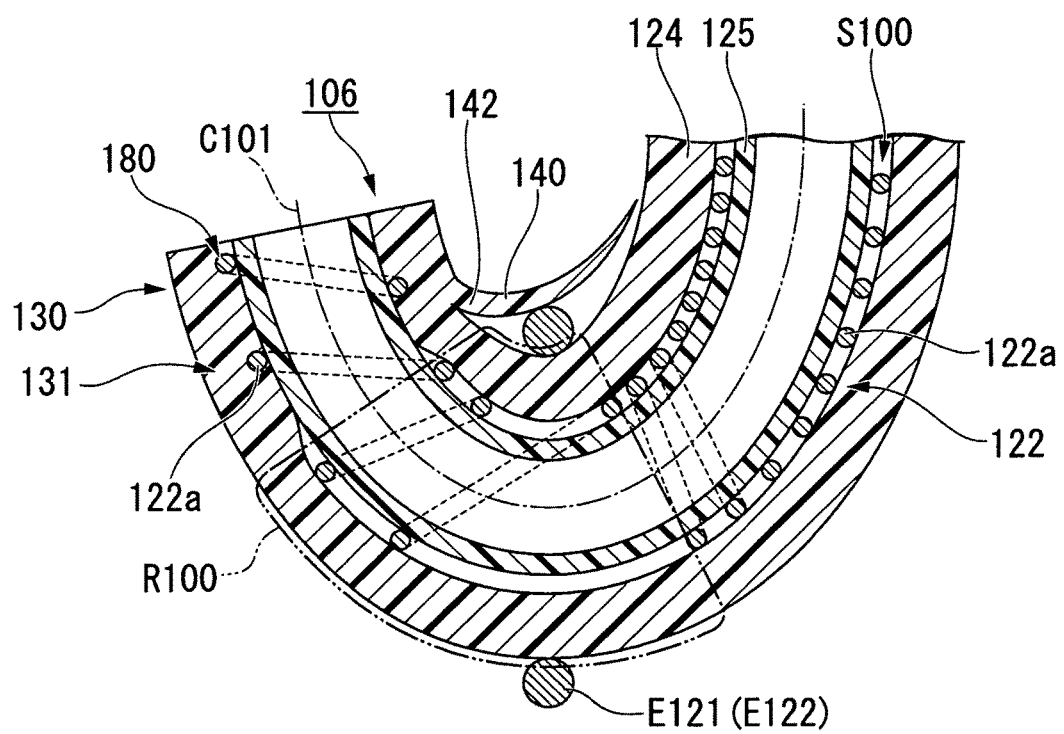
FIG. 25 is a cross-sectional view showing a state in which the stent for medical use according to the fifth embodiment of the present invention is folded back by a snare.

In the stent 106 according to the embodiment with such a configuration, the loop portion E121 of the snare E120 is hooked to the gripping target region R100 as shown in FIG. 25 when the stent is extracted after the stent is indwelled. When the snare E120 is pulled back, the outer layer 124 which is pressed by the wire E122 is deformed toward the longitudinal axis C101, and the stent 106 is folded back at the gripping target region R100. The first strand 122a which is located at the position of the wire E122 in the direction along the longitudinal axis C101 moves inside the gap S100 to be separated from the wire E122. The first strand 122a moves in the same way inside the gap S100 even when the stent 106 is bent.

Since the outer layer 124 and the inner layer 125 may be deformed without moving along with the movement of the first strand 122a inside the gap S100, the outer layer 124 and the inner layer 125 are not easily broken. Accordingly, the buckling resistance of the stent 106 increases.

According to the stent 106 of the embodiment, the stent may maintain a space inside a tube conduit in the indwelled state. Further, the stent may be easily crushed, that is, deformed, during the extraction operation.

According to the stent 106 of the embodiment, the first strand 122a is formed to be movable in the direction along the longitudinal axis C101 inside the gap S100 between the outer layer 124 and the inner layer 125. For this reason, the inner layer 125 and the outer layer 124 are not easily broken when the snare E120 is hooked or bent at the gripping target region R100.

In the embodiment, the gap S100 between the outer layer 124 and the inner layer 125 is formed in the direction along the longitudinal axis C101 from the proximal end portion 142 of the flap 140 to the center portion 124a of the outer layer 124. However, the gap S100 may be formed from the proximal end portion 142 of the flap 140 to the boundary position Q100 in the direction along the longitudinal axis C101. In such a configuration, the first strand 122a may move inside the gap S100 in the direction along the longitudinal axis C101 when the snare E120 is hooked to the gripping target region R100.

While the second to fifth embodiments of the present invention have been described with reference to the drawings, the detailed configuration is not limited to the embodiments.

Figure 26:
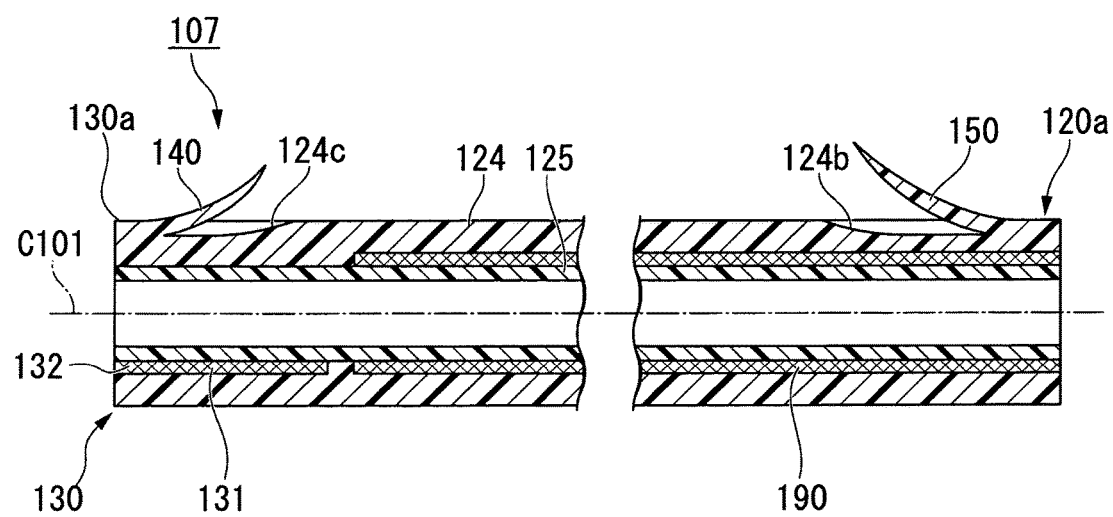
FIG. 26 is a side cross-sectional view showing a stent for medical use according to a modified example of the embodiment of the present invention.

For example, in the second to fifth embodiments, the coil 122 is used as the first reinforcement portion, but the first reinforcement portion may be a blade 190 as in a stent 107 (a stent for medical use) shown in FIG. 26. The blade 190 has a known configuration in which a metallic strand is woven in a mesh shape.

In the second to fifth embodiments, the snare E120 is used to extract the stent to the outside of a body. However, the stent may be extracted by gripping the gripping target region R100 of the stent or hooking the proximal end portion 142 of the flap 140 with a gripping forceps instead of the snare E120.

In the second to fifth embodiments, three flaps 150 are provided in the outer layer 124 of the stent, but the stent may not include the flaps 150.

In the second to fifth embodiments, an example is shown in which the flap 140 is formed by notching and raising. However, the flap 140 may be formed by fixing a member formed separately from the outer layer 124 to the outer layer 124 by thermal welding or the like. The same also applies to the flap 150.

In the second to fifth embodiments, a case has been described in which the stent is indwelled inside the bile duct P103. However, the stent according to the embodiment may be used while being indwelled inside a pancreas duct.

While the embodiments of the present invention have been described, the technical scope of the present invention is not limited to the above-described embodiments. That is, the combination of the components of the embodiments may be changed or the components may be omitted or modified in various forms within the scope without departing from the spirit of the present invention. The invention is not limited to the description above, and is limited only by the appended claims.

What is claimed is:

1. A stent for medical use comprising:
  a main body that includes:
    a first end; and
    a second end, the main body being formed from a resin material and in a tubular shape along a longitudinal axis from the first end to the second end;
  a first engaging member that includes a first fixation end positioned on an outer circumference surface of the main body at the first end side of the main body and a first free end positioned a distance away from the outer circumference surface of the main body in a radial direction of the main body, the first engaging member extending from the first fixation end to the first free end; and
  a wire that includes a first end and a second end and is formed from a material having an elastic modulus greater than an elastic modulus of the resin material, the wire wound about the longitudinal axis in a spiral shape from the first end of the wire to the second end of the wire, and the wire being implanted between an inner circumference of the main body and an outer circumference of the main body,
  wherein, in the longitudinal axis direction:
    the first end of the wire is positioned between the second end of the wire and the first end of the main body,
    a length between the first end of the wire and the first end of the main body is longer than a length between the second end of the wire and the second end of the main body, and
    a length between the first end of the wire and the first fixation end is equal to or longer than a length between the first end of the main body and the first fixation end.

2. The stent for medical use according to claim 1, wherein the first engaging member is provided between the first end of the wire and the first end of the main body in a direction along the longitudinal axis of the main body, and fixed to the outer circumference surface.

3. The stent for medical use according to claim 1,
wherein the first end of the wire is provided at a position between the first fixation end and a center position of the main body along the longitudinal axis.

4. The stent for medical use according to claim 1, further comprising
a second engaging member which includes a second fixation end positioned on an outer circumference surface of the main body at the second end side of the main body and a second free end positioned at a distance away from the outer circumference surface of the main body in the radial direction, the second engaging member elongated from the second fixation end to the second free end,
wherein a length between the second fixation end and the second free end is longer than a length between the first fixation end and the first free end.

* * * * *